(12) United States Patent
Chahine

(10) Patent No.: US 10,535,278 B2
(45) Date of Patent: Jan. 14, 2020

(54) GARMENT WITH STRETCH SENSORS

(71) Applicant: Tony Chahine, Toronto (CA)

(72) Inventor: Tony Chahine, Toronto (CA)

(73) Assignee: MYANT, INC., Toronto (CA)

( * ) Notice: Subject to any disclaimer, the term of this patent is extended or adjusted under 35 U.S.C. 154(b) by 555 days.

(21) Appl. No.: 15/230,104

(22) Filed: Aug. 5, 2016

(65) Prior Publication Data
US 2017/0036066 A1 Feb. 9, 2017

Related U.S. Application Data

(60) Provisional application No. 62/201,429, filed on Aug. 5, 2015.

(51) Int. Cl.

| | |
|---|---|
| *G01L 9/00* | (2006.01) |
| *G09B 19/00* | (2006.01) |
| *A41D 1/00* | (2018.01) |
| *G06K 9/00* | (2006.01) |
| *A61B 5/11* | (2006.01) |
| *G16H 40/63* | (2018.01) |
| *G16H 20/30* | (2018.01) |

(Continued)

(52) U.S. Cl.
CPC ......... *G09B 19/0038* (2013.01); *A41D 1/002* (2013.01); *A61B 5/1116* (2013.01);
(Continued)

(58) Field of Classification Search
None
See application file for complete search history.

(56) References Cited

U.S. PATENT DOCUMENTS

| | | |
|---|---|---|
| 5,906,004 A | 5/1999 | Lebby et al. |
| 6,381,482 B1 * | 4/2002 | Jayaraman ............ A61B 5/6805 600/388 |

(Continued)

FOREIGN PATENT DOCUMENTS

| | | |
|---|---|---|
| CA | 2 525 525 A1 | 11/2004 |
| CA | 2 604 990 A1 | 4/2008 |

(Continued)

OTHER PUBLICATIONS

WIPO, International Search Report for International Application No. PCT/CA2016/000202, dated Sep. 19, 2016.

*Primary Examiner* — Paul M. West
*Assistant Examiner* — Mark A Shabman
(74) *Attorney, Agent, or Firm* — Haynes and Boone, LLP

(57) ABSTRACT

A knitted or woven garment configured for sensing movement of an adjacent underlying body portion of a wearer of the garment via one or more sensors, the garment including a garment body including a plurality of fibres knitted together to form a layer of the garment, the garment layer for positioning adjacent to the underlying body portion when worn by the wearer; one or more electrical connectors attached to the garment body, the one or more electrical connectors for facilitating receipt and transmission of electrical signals between a controller and the one or more sensors when the controller is connected to the one or more electrical connectors; a conductive pathway consisting of one or more conductive fibres incorporated in the garment layer by knitting as part of the plurality of fibres, the conductive pathway electrically connected to the one or more electrical connectors and to the one or more sensors; each of the one or more sensors incorporated in the garment layer by knitting as part of the plurality of fibres, each of the one or more sensors knitted using a plurality of conductive fibres electrically connected to the one or more conductive fibres of the conductive pathway; wherein the controller is configured to measure changes in at least one of resistance or capacitance of the one or more sensors as representative of the movement of the underlying body portion when positioned adjacent to the one or more sensors.

24 Claims, 11 Drawing Sheets

(51) Int. Cl.
*A61B 5/00* (2006.01)
*A61B 5/113* (2006.01)

(52) U.S. Cl.
CPC .......... *A61B 5/1121* (2013.01); *A61B 5/1126* (2013.01); *A61B 5/4519* (2013.01); *A61B 5/486* (2013.01); *A61B 5/4854* (2013.01); *A61B 5/6804* (2013.01); *A61B 5/74* (2013.01); *G06K 9/00342* (2013.01); *G16H 20/30* (2018.01); *G16H 40/63* (2018.01); *A41D 2600/10* (2013.01); *A61B 5/1135* (2013.01); *A61B 2562/0261* (2013.01)

(56) References Cited

U.S. PATENT DOCUMENTS

| | | | |
|---|---|---|---|
| 7,712,373 B2 | 5/2010 | Nagle et al. | |
| 8,161,826 B1 * | 4/2012 | Taylor | G01L 1/18 73/862.044 |
| 8,298,968 B2 * | 10/2012 | Swallow | D03D 1/0088 345/173 |
| 8,536,075 B2 * | 9/2013 | Leonard | D02G 3/441 313/511 |
| 2006/0281382 A1 * | 12/2006 | Karayianni | D03D 1/0088 442/181 |
| 2011/0010001 A1 | 1/2011 | Chung et al. | |
| 2013/0176737 A1 * | 7/2013 | Zhou | H05K 1/038 362/249.06 |
| 2015/0075303 A1 * | 3/2015 | Connor | A61B 5/1126 73/865.4 |

FOREIGN PATENT DOCUMENTS

| | | |
|---|---|---|
| WO | WO 2003/060449 A1 | 7/2003 |
| WO | WO 2014/138204 A1 | 9/2014 |
| WO | WO 2015/013615 A2 | 1/2015 |

* cited by examiner

GARMENT WITH STRETCH SENSORS

CROSS-REFERENCE TO RELATED APPLICATIONS

This application claims the benefit of, and priority to, U.S. Provisional Patent Application No. 62/201,429, filed Aug. 5, 2015, the entire contents of which is hereby incorporated herein by express reference thereto.

TECHNICAL FIELD

The present invention relates to garments with sensors.

BACKGROUND

A central learning point for garment wearers during certain activities is to become able to sense, what the body is doing: which muscles are flexed? Are the joints aligned? Am I stretching the sides of my body? Do I push the shoulder blades into the spine? For a new or medium skilled garment wearer learning a new activity (e.g. sport) this is difficult to learn. The method for learning this is to have a teacher watching the student while performing specific positions. The teacher will then give instructions and corrections. The teacher might put pressure to the part of the body that should be activated in order for the student to feel the part of the body. The teacher also often ties a belt around a specific part of the body to make the student aware of the movements of that body part. Based on these instructions it is then up to the student to be able to activate the same parts of the body while practicing without the teacher. The shortcoming of this method is that the teacher can't be around every time the student practices. The advantage of this method is that the teacher is able to evaluate every part of the body with just one glance, recognizing which parts of the body are stretching, which are flexed, which joints are aligned, and if there is a symmetry in the movement.

Other needs in the areas of medicine and rehabilitation or physiotherapy is for tracking of movements of specific body parts, in particular for range of motion for recuperation therapies, as well as for swelling/enlargement of body parts due to disease or other medical conditions. Again, historical tracking of body movement is needed to facilitate treatment in these areas, however current movement sensing clothing is cumbersome at best. For example, placement of particular sensors (e.g. stretch sensors) adjacent to specified body parts can be difficult due to repeatable positioning difficulties of the sensors, as well as maintaining of the sensors in position during the body movements being tracked/monitored.

SUMMARY

A knitted garment configured for sensing movement of an adjacent underlying body portion of a wearer of the garment via one or more sensors, the garment comprising: a garment body including a plurality of fibres knitted together to form a layer of the garment, the garment layer for positioning adjacent to the underlying body portion when worn by the wearer; one or more electrical connectors attached to the garment body, the one or more electrical connectors for facilitating receipt and transmission of electrical signals between a controller and the one or more sensors when the controller is connected to the one or more electrical connectors; a conductive pathway consisting of one or more conductive fibres incorporated in the garment layer by knitting as part of the plurality of fibres, the conductive pathway electrically connected to the one or more electrical connectors and to the one or more sensors; each of the one or more sensors incorporated in the garment layer by knitting as part of the plurality of fibres, each of the one or more sensors knitted using a plurality of conductive fibres electrically connected to the one or more conductive fibres of the conductive pathway; wherein the controller is configured to measure changes in at least one of resistance or capacitance of the one or more sensors as representative of the movement of the underlying body portion when positioned adjacent to the one or more sensors.

A woven garment configured for sensing movement of an adjacent underlying body portion of a wearer of the garment via one or more sensors, the garment comprising: a garment body including a plurality of fibres woven together to form a layer of the garment, the garment layer for positioning adjacent to the underlying body portion when worn by the wearer; one or more electrical connectors attached to the garment body, the one or more electrical connectors for facilitating receipt and transmission of electrical signals between a controller and the one or more sensors when the controller is connected to the one or more electrical connectors; a conductive pathway consisting of one or more conductive fibres incorporated in the garment layer by weaving as part of the plurality of fibres, the conductive pathway electrically connected to the one or more electrical connectors and to the one or more sensors; each of the one or more sensors incorporated in the garment layer by weaving as part of the plurality of fibres, each of the one or more sensors woven using a plurality of conductive fibres electrically connected to the one or more conductive fibres of the conductive pathway; wherein the controller is configured to measure changes in at least one of resistance or capacitance of the one or more sensors as representative of the movement of the underlying body portion when positioned adjacent to the one or more sensors.

A fabric garment configured for sensing movement of an adjacent underlying body portion of a wearer of the garment via one or more sensors, the garment comprising: a garment body including a plurality of fibres interlaced together to form a layer of the garment, the garment layer for positioning adjacent to the underlying body portion when worn by the wearer; one or more electrical connectors attached to the garment body, the one or more electrical connectors for facilitating receipt and transmission of electrical signals between a controller and the one or more sensors when the controller is connected to the one or more electrical connectors; a conductive pathway consisting of one or more conductive fibres incorporated in the garment layer by interlacing as part of the plurality of fibres, the conductive pathway electrically connected to the one or more electrical connectors and to the one or more sensors; each of the one or more sensors incorporated in the garment layer by interlacing as part of the plurality of fibres, each of the one or more sensors interlaced using a plurality of conductive fibres electrically connected to the one or more conductive fibres of the conductive pathway; wherein the controller is configured to measure changes in at least one of resistance or capacitance of the one or more sensors as representative of the movement of the underlying body portion when positioned adjacent to the one or more sensors.

BRIEF DESCRIPTION OF THE DRAWINGS

The non-limiting embodiments may be more fully appreciated by reference to the following detailed description of the non-limiting embodiments when taken in conjunction with the accompanying drawings, by example only, in which.

DETAILED DESCRIPTION OF THE EMBODIMENTS

It will be appreciated that for simplicity and clarity of illustration, where considered appropriate, numerous specific details are set forth in order to provide a thorough understanding of the exemplary embodiments described herein. However, it will be understood by those of ordinary skill in the art that the embodiments described herein can be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the possible implementations of various embodiments that can be varied as known by a person skilled in the art.

A central learning point for yoga students (as well as other sports or activities including movement of specified body parts or regions) is to become able to sense, what the body is doing: which muscles are flexed? Are the joints aligned? Am I stretching the sides of my body? Do I push the shoulder blades into the spine? For a new or medium skilled yoga (e.g. sport/activity) student this is difficult to learn. The method for learning this is to have a teacher (or medical practitioner such as a nurse or physiotherapy) watching the student while performing specific positions. The teacher will then give instructions and corrections. The teacher might put pressure to the part of the body portion or region that should be activated in order for the student to feel the part of the body. The teacher also often ties a belt around a specific part of the body to make the student aware of the movements of that body part. Based on these instructions it is then up to the student to be able to activate the same parts of the body while practicing without the teacher. The shortcoming of this method is that the teacher can't be around every time the student practices. The advantage of this method is that the teacher is able to evaluate every part of the body with just one glance, recognizing which parts of the body are stretching, which are flexed, which joints are aligned, and if there is a symmetry in the movement.

Figure 1:
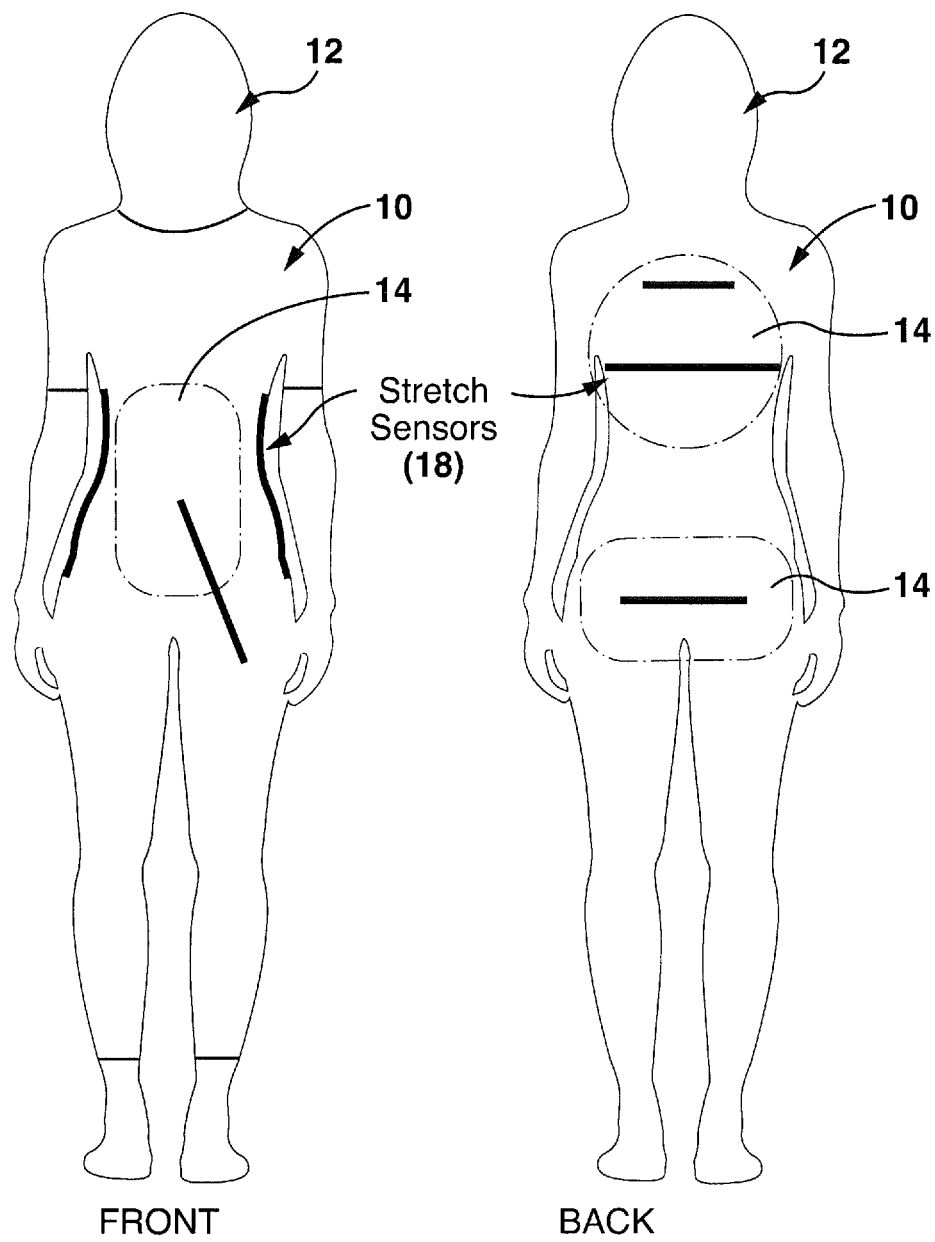
FIG. 1 is an example of a garment with sensors.

Disclosed herein is a system combining clothing and microelectronics—it is a wearable garment 10 (see FIG. 1). The disclosed system can integrate electronics and a full body garment, and can target the yoga domain specifically, or other activities with associated movement as desired. Aims for yoga students 12 (e.g. garment wearer) are, to be able to lift and stretch the entire body (or body portions 14) by activating the right muscles, and to achieve alignment, resulting in a healthy posture and reduction of the pressure on the inner organs, which would come from a posture where the person is not activating the muscles, stretching and lifting the body portions 14. When practicing yoga a central goal is to learn how to keep this lifted posture, and then to maintain it throughout the day—even while not practicing yoga.

The garment 10, e.g. a textile-based product, can be used by a user 12 (such as, a human). The garment 10 includes (and is not limited to) any one of a knitted textile, a woven textile, or a cut and sewn textile, a knitted fabric, a non-knitted fabric, a material that may or may not contact the user, a mat, a pad, a seat cover, etc., in any combination and/or permutation thereof (any equivalent thereof). The garment 10 can include an integrated functional textile article. It will be appreciated that some embodiments described a knitted garment, and it is understood that these embodiments may be extended to any textile fabric forms and/or techniques such as (weaving, knitting—warp, weft etc.), and the embodiments are not limited to a knitted garment. It will be appreciated that (where indicated) the FIGS. (drawings) may be directed to a knitted garment body layer 23, and it will be appreciated that the knitted garment body layer 23 is an example of any form of textile fabrics forms and techniques such as (weaving, knitting—warp, weft etc.) for the garment body layer 23, and that any description and/or illustration to the knitted garment fabric does this limit the scope of the present embodiments. In accordance with an embodiment, there is provided a garment 10 made with any textile forming technique (and the knitted fabric garment is simply an example of such an arrangement).

Figure 2:
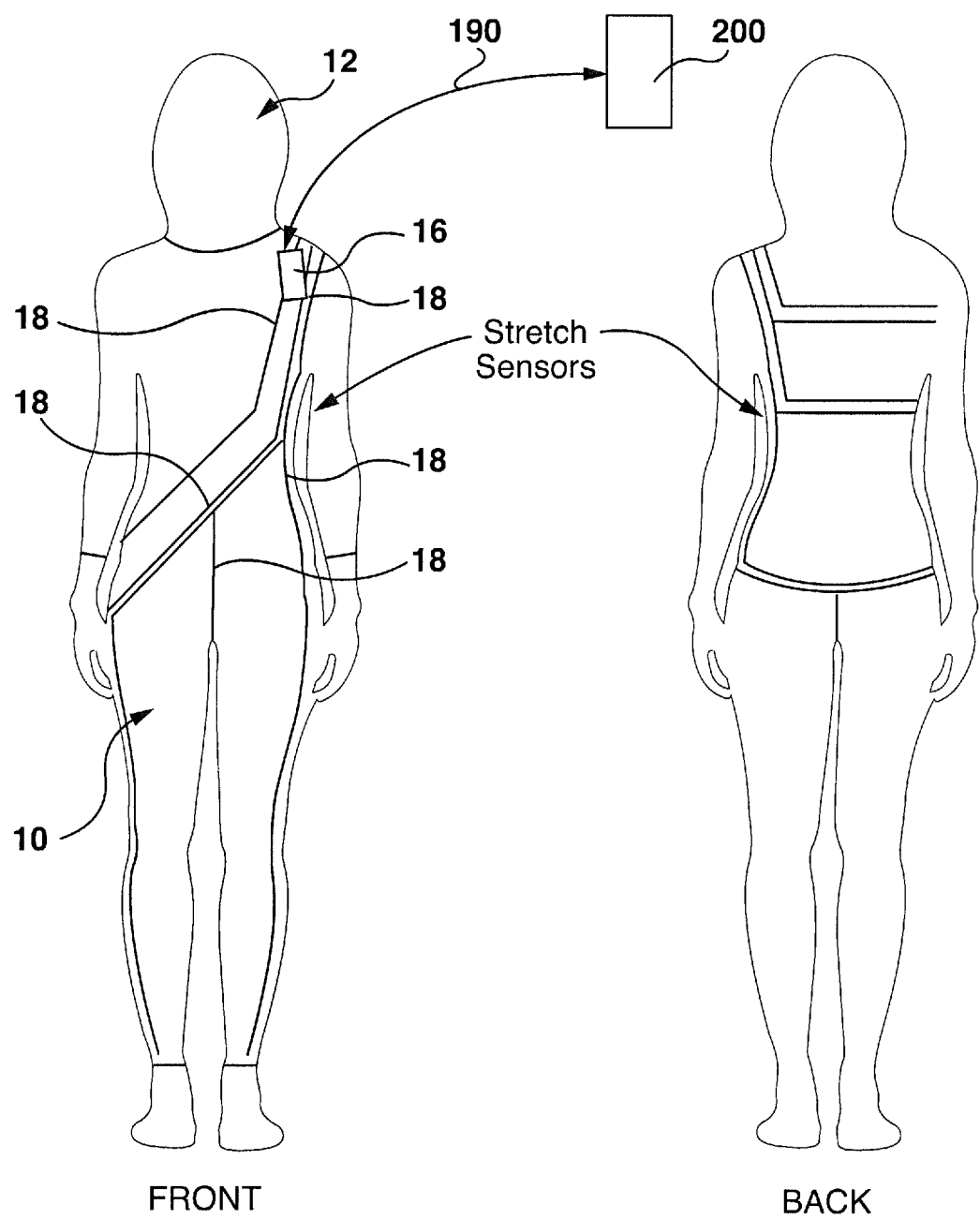
FIG. 2 is a further embodiment of the garment of FIG. 1 showing communication with a communication device.

Disclosed herein is a system that helps yoga students (e.g. garment wearers 12) learn to sense if they are making the right movements to achieve alignment, and stretching and lifting of the body portion(s) 14. Doing this can assist yoga students to improve their practice by giving them feedback concerning their progress and by giving them instructions while practicing. Accordingly the system can include a digital yoga teaching and yoga performance (or other activities) evaluation tool 200 (see FIG. 2) which can interact with a controller 16 connected to the knitted garment 12 further described below. The system can be a digital supplement to the teacher (or medical practitioner), helping to improve the body posture.

The system disclosed herein addresses new or medium skilled yoga students (or other activities) needing teachers to watch them practice, in order to learn how to feel if the body is moving correctly; which is not so easy, since the teacher is not around all of the time yoga practicing is taking place. A yoga student (garment wearer) typically needs to practice at home between yoga classes, which means that she is in a situation where she needs the help of the teacher, but he is not available.

The system disclosed herein offers an integrated solution able to recognize the posture of the student (garment wearer 12) and communicate suggestions for improvements. Disclosed is a yoga suit (garment 10) with integrated stretch sensors 18 able to measure the body posture of the student 12, and give the student real time feedback for improvements. The system can use stretch sensors 18 integrated in a yoga suit 10 to measure yoga movements and yoga postures (i.e. movements due to activities) via readings obtained from the sensors 18 due to movements of specific body parts or regions 14 adjacent to the sensors 18 in the knitted garment 10. It can then collect the measurements in a small electronic device 16 (e.g. printed circuit board or PCB) mounted in the yoga suit 10 and send the measurements through a wireless connection 190 (or other wired connection) to an application 201 (see FIG. 9) running on a mobile device (e.g. smartphone or tablet 200). Via the application 201 the yoga student 12 can receive instructions or feedback. Measuring yoga postures via the sensors 14, it is important to realize, that it could be too large a task to aim for a suit 10 covering all possible yoga postures and all muscles involved. With this point of departure the present system has been developed based on a dialogue with Iyengar yoga teachers regarding body parts 14 used in yoga postures. If these body parts 14 are worked well by the yoga student 12, she can have a good core muscle activity, supporting her posture. Non-limiting examples of postures (e.g. movements) that can be measured by the present system include: (i) the upper torso (chest, back, shoulders) 14: here the system can measure the ability to lift the chest 14 and press the shoulder blades 14 into the body in the direction of the spine 14; (ii) the sides of the torso (side ribs) 14: the system can measure the ability to increase the length of the side of the body (from the upper hip until the armpits) 14: and (iii) the hips/pelvis 14: the system can measure the ability to position the front and backside of the pelvis 14 in line (horizontal) by rolling the inner part of the thighs 14 backwards, lifting the pubic bone 14 towards the navel 14 and rolling the buttocks 14 down.

The measurements can be communicated to the student 12 via for example a tablet or smartphone 200. The algorithms 201 running on the tablet/smartphone 200 can compare the posture of the student 12 with previous postures, and accordingly also state if the student 12 is improving. Information of the sensors 18 can be communicated visually via a display of an electronic device 200 running the application 201 and can be used by the student 12 after or before practicing the movements of the activities (e.g. yoga) as a way of evaluating performance. Therefore the system can help a new or medium skilled yoga student 12 to learn to feel if the body parts 14 are moving correctly, and to understand if she is improving doing what she is doing, or if she is on the wrong track.

The system disclosed herein can use stretch sensors 18 mounted in a specially designed suit 10, placed on selected parts of the body 14 in order to communicate (e.g. to a student 12) if the body in total is aligned (e.g. spine, pelvis 14) and if it is stretching (e.g. including the elongation of the sides 14 of the body), and if it is lifting (e.g. including the pressuring of the shoulder blades 14 into the spine 14 and the positioning of the pelvis 14). From selected measuring points the system can infer if the body has a healthy posture and if it is actively lifted. For example, from the stretching of the stretch sensors 18 (e.g. operably connected to a garment 10 according to the invention) it can be inferred that the muscles 14 are flexed, since stretching would not be possible without flexing the muscles 14. Accordingly the stretch sensors 18 can measure muscle flexing/activity of muscles 14 which occurs during yoga. The system can also, based on experience of yoga teachers (e.g. programmed into memory of a mobile device 200 accessible to an application 201 running on the mobile device 200), infer that the right position for the entire body is achieved when all the sensors 18 connected to the garment 10 are stretched, since it would not be possible to stretch them and hold a wrong position.

The concept for measuring posture, which can be applied in the presently disclosed system, can also form the base of developing new products for measuring posture, which focus on the core muscles 14 and the stretching of the body 14 and not primarily the position of the skeleton.

In an embodiment, the present system facilitates measuring of body activity (for any appropriate activity such as yoga or another sport by example only) by operably connecting sensors 18 to a garment 10 which makes it possible to measure for example alignment, stretching (e.g. of body sides) 14, lifting of the body (e.g. of the pelvis, shoulder blades) 14, activation of muscles 14 central to core alignment in yoga (e.g. by combining information from multiple sensors 18 as collected via the controller 16 coupled to the mobile device 200).

In another embodiment, the present system incorporates a garment 10 having a construction which facilitates it to move like the skin and with the skin (i.e. not sliding on top of the skin) of a wearer 12. For example, the design of the garment 10 (e.g. fabric quality and stretchability), can facilitate the garment 10 to move like the skin and with the skin (i.e. not sliding on top of it) of a wearer 12. For example, the construction and application method of the wires (e.g. fibres) of one or more electronic circuits 19 attached to the suit 10 can facilitate communication with the sensors 18 experiencing stretching to closely approximate the stretching of the fabric (i.e. body) of the suit 10, thereby providing for a garment 10 that moves with the skin of a wearer 12. Further, the application method of the stretch sensors 18 can facilitate them to move like the fabric of the suit 10, following the skin.

For example, measuring of the alignment, stretching and lifting of the body portions/regions 14 can be performed by measuring the following places 14 on the body with a stretch sensor 18: (i) the upper torso 14: for example a sensor 14 can be placed horizontally on the back of the suit 10 between the shoulder blades 14. Alternatively, the sensor 18 can be placed with a starting point on the one shoulder blade 14, and can move around the chest 14 and end at the other shoulder blade 14; (ii) the sides of the torso 14: a sensor 18 can be placed vertically on each side 14 of the torso from the upper hip 14 to the armpit 14; (iii) the hips/pelvis 14: a sensor 18 can be placed diagonally from the upper part of the front thigh 14 to the navel 14, and a sensor 18 can be placed horizontally on the lower part of the buttocks 14 from one buttock 14 to the other 14 (e.g. in some embodiments approximately a distance of 6 cm).

Figure 6:
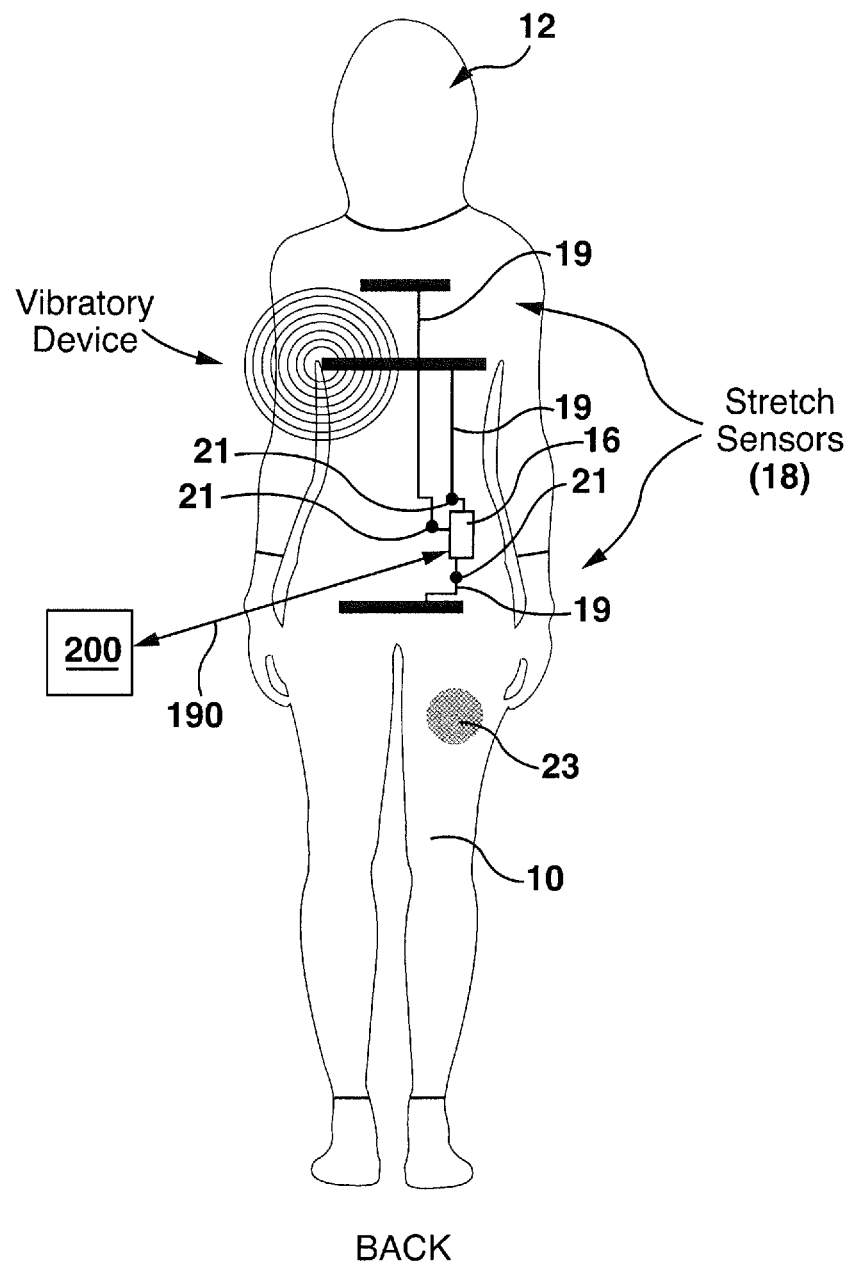
FIG. 6 shows a further embodiment of the garment of FIG. 1 with vibration.

The communication of the measurements to the yoga student 12 can take place over a smart phone or tablet 200. There can at least be the following features of the application 201 for reporting to the wearer 12: (i) a calibration of the suit/person 12 wearing the suit 10; and (ii) two interaction modes: 1) by sound emitted by the device 200 and/or the controller device 16 for guiding while performing the exercises (this calls for real-time calculations); and 2) a visualization of the performance and progression over time for retrospective evaluation as displayed on the display of the device 200, as processed and output by the application 201 based on receipt and processing of the sensor 18 readings as collected via the conductive pathways 19 of electronic circuits connecting the sensors 18 to the controller 16 (e.g.

via an electrical connector 21 fastened to the garment body 23 of the garment 10—see FIG. 6).

The suit 10 can be tight, have long legs (alternatively short legs is also an option), no arms and have a high boat formed neckline, as desired. The suit 10 can also be formed (e.g. knitted) as a seamless one piece garment 10 or can be assembled as a plurality of knitted panels stitched to one another. It is recognised that in one embodiment, the knitted garment 10 can have a knitted fabric layer which has knitted therein the sensors 18 (a plurality of conductive/non-conductive threads in a sensor pattern) as well as the conductive pathway 19 (a plurality of conductive/non-conductive fibres).

Also, the sensors 18 can be placed on the inner side of the suit 10 in pockets protecting the sensors 18 but allowing them to move freely, as such providing for sensors 18 that are not integrated into the fabric layer of the garment 10. Examples of sensor 18 attachment adjacent to, rather than embedded in, the garment body layer 23 of the garment 10 fabric can include; topstitching of the patch sensor on top of the garment body layer 23, sewing of a sensor layer patch adjacent to the garment body layer 23 (as an overlying sensor patch), and/or bonding (e.g. via adhesive) of the sensor to the garment body payer 23 and/or directly to the body of the wearer 12. The quality of the fabric and the details of the design can provide that the suit 10 moves like the skin, based on the weaving or knitting pattern of the fabric fibres composing the plurality of fibres in the garment body layer 23. The suit 10 can be made as a cut-and-sew or a seamless.

The electric cords/fibres (i.e. conductive pathways 19) can be placed on (i.e. knitted as part of the plurality of fibres in the garment body layer 23) the sides of the suit 10, and crossing it where attached to the sensors 18. The PCB (i.e. controller 16) can be just below the shoulder 14 on the front of the suit 10, for example, in order to make sure that it will not be in the way of the activity (e.g. yoga exercise).

Figure 7:
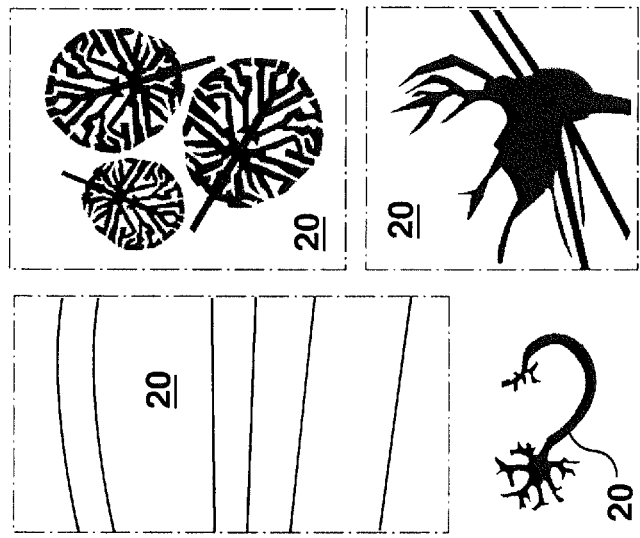
FIG. 7 shows a further embodiment of the garment of FIG. 1 with patterns.
Figure 7:
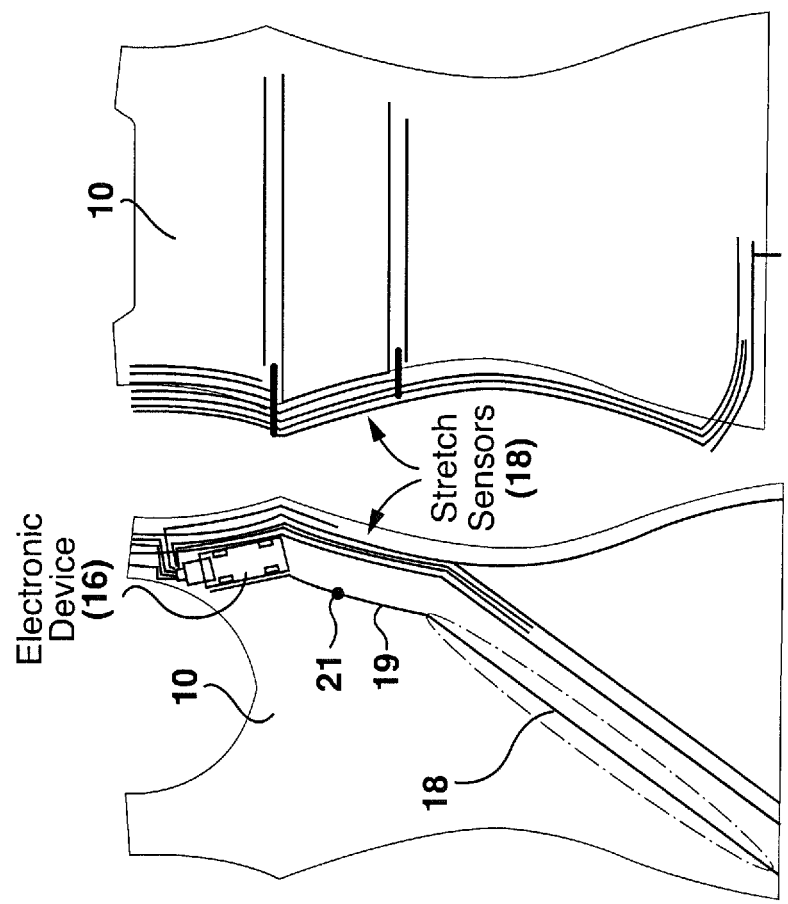
Figure 8:
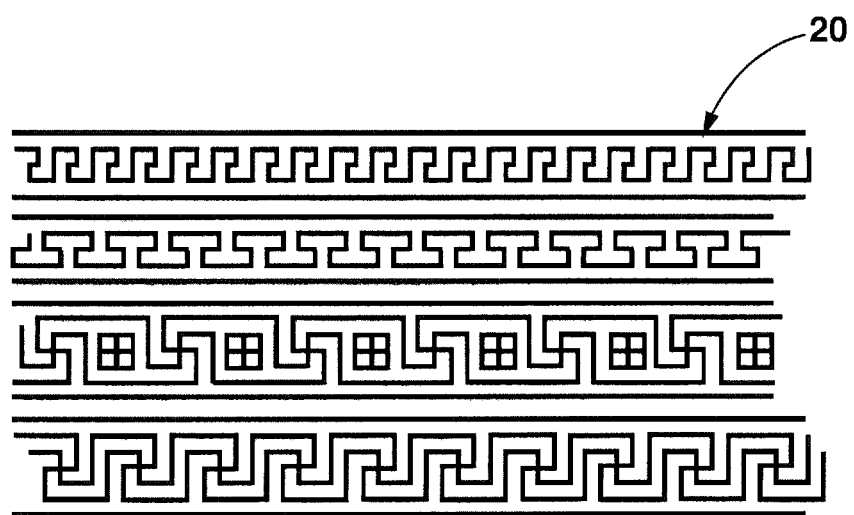
FIG. 8 shows an example fabric sensor of the garment of FIG. 1.

The application method of the cords/fibres making up the sensors 18 and/or the conductive pathways 19 can be adapted for a design that moves like the skin, accordingly the cords/fibres/wiring of suit components 18,19 can also move like the skin. The cords/fibres/wiring can be made in a stretchable pattern inspired by a meander band-pattern 20 (see FIG. 8), for example. The cords/fibres/wiring can be applied to the suit 10 with different aesthetic inspirations 20, as desired (see FIG. 7). The cords/fibres/wiring can also inspired by specific colour combinations.

In one embodiment, the suit 10 can be tested for its ability to move like the skin, and it can be concluded that the design accomplishes that. The tests have been done by applying sensors 18 directly to the skin, and then doing exercises wearing the skin-mounted sensors 18 and the suit 10 with mounted sensors 18 on top of the garment body layer 23. The skin-mounted sensors 18 show the movement of the skin, while the suit 10 mounted sensors 18 show the movement of the suit 10. When the two sensors 18 produce similar outputs, it shows that the suit 10 moves like the skin.

The system can have multiple operation scenarios. A first operation scenario can be used during yoga class (e.g. activity) with the purpose of after class evaluation: The yoga student 12 can wear the IT Kosha suit 10 while attending class. Before the class begins she can start the IT Kosha application 201 on her phone 200. The student 12 need not consciously interact with the IT Kosha application 201 again, before she exits from the class and turns the application 201 off. But while attending class the IT Kosha application 201 can measure the yoga student's 12 postures. This can be done with for example 5 mounted/embedded stretch sensors 18 in/of the suit 10. The data from the sensors 18 can be collected in the small PCB 16 integrated in the suit 10 via attachment with the connector(s) 21 (see FIG. 6). The data are sent from the PCB 16 to the yoga student's smartphone 200 with Bluetooth 190.

After class the yoga student 12 can get feedback on her performance. For example, she wants to see how well her alignment was, and how well she was able to lift the body 14 and stretch the sides of the body 14. She can open the IT Kosha application 201 and enter the evaluation mode via the user interface of the device 200. In this mode she can see a comparison of today's yoga postures on the display and the last time she made the same postures (alternatively the comparison can be with the best posture she has made within the last ½ year, i.e. historical).

A second operation scenario can be used while practicing alone as an assistant teacher. For example, the yoga students 12 can want to practice yoga at home. She can put on the IT Kosha suit 10 and open the IT Kosha application 201 on her smartphone 200; she can select "teacher assistant" via the user interface. She can start doing yoga postures (e.g. activities). The machine learning software 201 integrated in the IT Kosha solution can recognize which postures she makes. The application 201 can give her instructions via the user interface for performing the yoga postures correctly— e.g. it can say "stretch the sides of the body 14 and hook the side ribs 14 like the claws of a tiger" if the yoga student 12 is entering the pose Sirsasana (head balance), as detected by the sensors 18. As such, the application 201 can be programmed to recognize certain movements/positions of certain activities based on the sensor 18 readings collected by the device 16 due to movements performed by the various body regions 14 associated with the sensors 18 (e.g. aligned adjacent to the sensors 18 of the suit 10).

The stretch sensor 18 used in the IT Kosha garment 10 can be replaced by other types of stretch sensors 18, as desired.

The application of the stretch sensors 18 to the body 14 can also be achieved by attaching them to a belt or band instead of integrating them in a suit 10, as desired.

Another type of communication of the measurement results can also be considered. For example it would be a possibility to integrate a more tactile type of feedback to the user 12 via the user interface of the device 200 coupled to the device 16 connected to the suit 10, instead of communicating visually and audibly through the smartphone 200.

Described is a system and method of using a specific placement of stretch sensors 18 in order to measure alignment, stretching and lifting of the body 14, with the purpose of achieving a healthy posture (e.g. activity), by activating the core muscles 14. The idea of measuring body posture as stretching, lifting and alignment is not seen in the other products on the market.

The system can include a suit 10 with integrated tactile feedback e.g. vibration via the user interface of the device 200. Tactile feedback can facilitate feedback directly in the suit 10, e.g. via the controller device 16 for example, which is another type of communication than the above described.

Figure 5:
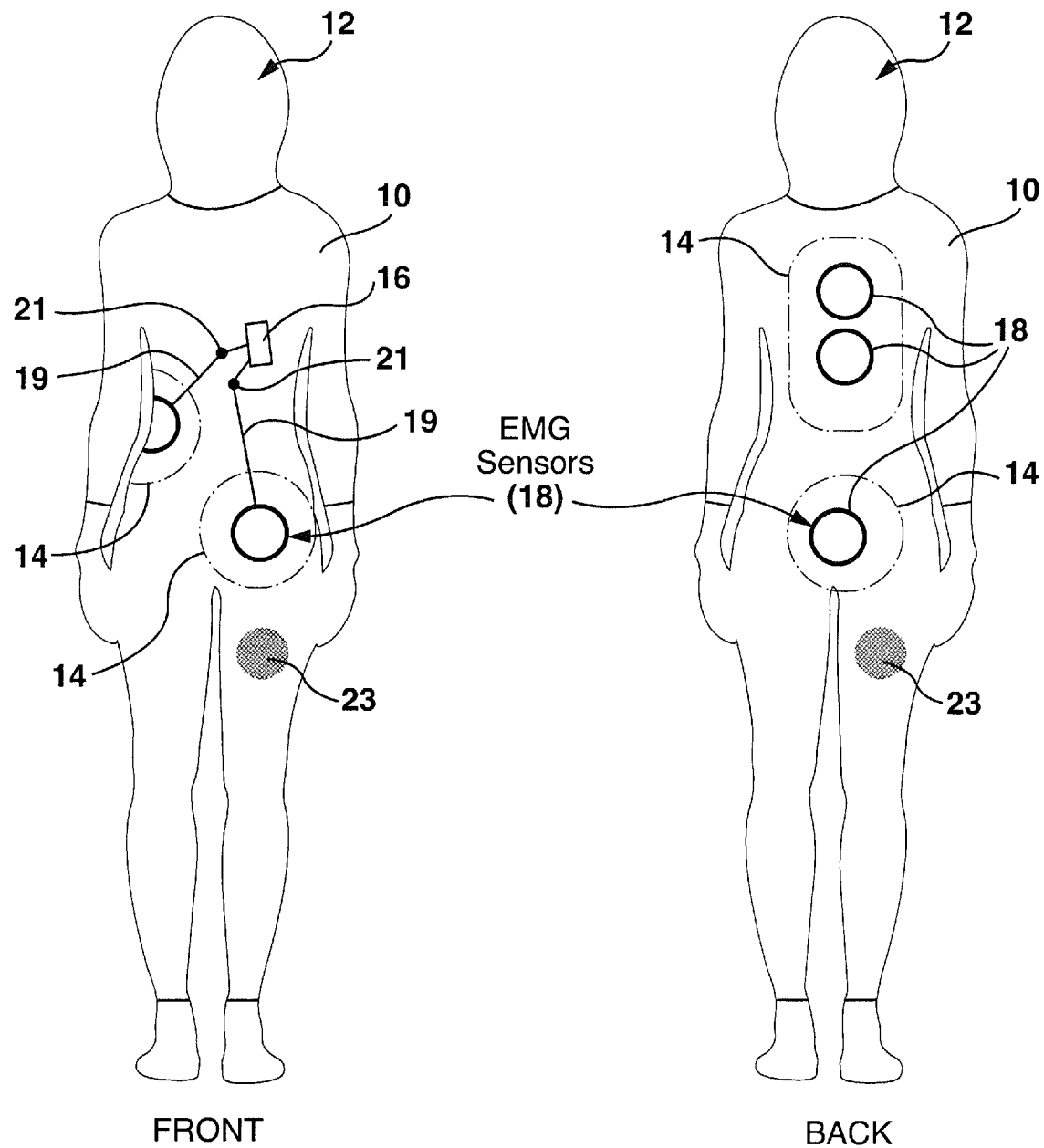
FIG. 5 shows a further embodiment of the garment of FIG. 1 for EMS sensors.

EMG-sensors 18 (see FIG. 5) can be used instead of or in addition to stretch sensors 18 to measure muscle 14 activity. EMG sensors 18 can be placed at the same positions 14 as stretch sensors 18.

The system disclosed herein can be implemented by a person 12 executing any sport or physical activity (e.g. yoga) to measure and track positioning and movement of the person's body 14 during the activity. The system can include a garment 10 (e.g. yoga suit or a belt/band) comprising one or more sensors 18 (e.g. stretch sensors) attached or otherwise embedded to/into fabric of the garment body layer 23 for measuring body activity (e.g. movement of a skin surface and/or muscle 14 activity) of a wearer 12 of the garment 10 (e.g. yoga student). Body activity information collected by the sensors 18 can be sent by the sensors 18 via wires or cords (e.g. conductive pathway 19) to an electronic device (e.g. PCB) 16 attached via the electrical connectors 21 such as but not limited to snap type connectors (to fabric of the garment body layer 23 for transmitting (e.g. via a wireless network module 16) the information as sensor data to a computing device 200 (e.g. mobile device of the yoga student 12). The computing device 200 can include a processor for running an application 201 (e.g. yoga application) capable of interpreting the sensor 18 data. For example, the application 201 can process the sensor 18 data to derive an activity map representative of which muscles 14 were activated by the student 12 during a particular yoga posture, the degree of activation of each muscle 14 that was activated, and the timing of activation of each muscle 14 during the posture. The application 201 can compare the representations of muscle 14 activity in the activity map to a standard activity map stored in a memory of the computing device 200 representative of an ideal or correct pattern of muscle 14 activity for the particular yoga posture. The results of the comparison can be displayed on a user interface of the computing device 200 for viewing by the yoga student 12 to receive feedback regarding which aspects of the posture were performed correctly and/or incorrectly, and/or to be coached on how to improve future performance of the yoga posture.

Garment 10

The garment 10 can be a form-fitting garment comprising textile (e.g. fabric) that has a plurality of knitted or woven fibres comprising the garment body layer 23, one or more sensors 18 attached or otherwise integrated into the garment body layer 23 by knitting to the textile for positioning adjacent to a body surface 14 of a wearer 12 of the garment 10, an electronic device (e.g. controller 16) attached to the textile 10 for receiving body activity signals generated and transmitted by the sensors 18, and wires or cords (e.g. conductive pathway 19) operably connected via connectors 21 to the sensors 18 and electronic device 16 for carrying the signals between the sensors 18 and electronic device 16.

The garment 10 can be of any type typically worn by a user 12 while performing physical activity or exercises such as yoga. Non-limiting examples of garment 10 types according to the invention are shirts, pants, leotards, unitards, belts, bands, stockings, leggings, tights, bodysuits, yoga suits, socks, and undergarments. In one embodiment, a garment 10 can be a belt or hand capable of being wrapped or wound around any part 14 of the body. In another embodiment, a garment 10 can be a yoga suit.

In one embodiment the garment 10 can be a form-fitting garment. Herein the term "form-fitting" refers to the tendency of a garment to conform to the contours of the parts 14 of the body covered by the garment 10. Typically once a form-fitting garment is put on, the fabric (i.e. garment body layer 23) of the form-fitting garment 10 resists shifting/displacement with respect to an underlying skin surface covered by the garment 10. Further, typically the fabric of a form-fitting garment 10 is capable of stretching (e.g. containing knitted fibres for both regions 22 not containing sensors 18 and regions 24 containing sensors 18—see FIG. 3 although seamless construction with appropriate garment regions/sections 22,24 can also be used as desired) in response to and to the same extent as the stretching of an underlying skin surface 14. In one embodiment the design of the garment 10 is tight (i.e. form-fitting) with long legs, no arms and a high boat-formed neckline.

The garment 10 can include stitched (e.g. knitted or woven) textile (e.g. fabric or fabrics represented by a plurality of fibres) which is stretchable (e.g. elastic). In one embodiment the movement and/or stretching of a skin surface 14 of a wearer of the garment 10 induces a corresponding movement and/or stretching in an overlying portion 24 of the garment 10. Non-limiting examples of fibre fabrics which can be included in the garment 10 are cotton, spandex, nylon, and polyester. The textile 10 can be stitched with thread that is also stretchable. In one embodiment thread and textile which are adjacent in the garment 10 can stretch the same amount in response to the movement or stretching of a skin surface 14 underlying the adjacent thread and textile. As such, the fibres of the thread/textile can be electrically conductive or non-conductive depending upon which region 22,24 there are in of the garment body layer 23 as well as whether there are used to form the conductive pathway 19 and/or the sensors 18 (e.g. knitted sensors 18 embedded or otherwise incorporated in the garment body layer 23).

The garment 10 and the various regions 22, 24, as well as the sensors 18 and conductive pathways 19 can be stitched (e.g. knitted or woven) using any method known to a person skilled in the art of garment construction. For example, the garment 10 can be made with a cut-and-sew or seamless design. In one embodiment the garment 10 can be made by circular knitting. As such, in one embodiment, the knitted sections 22, 24 contain embedded therein the garment body layer 23 the knitted conductive pathways 19 with knitted sensors 18. As such, within or otherwise embedded in the garment body layer 23 pertains to the components 19,18 are knitted into the layer 23 as part of the plurality of fibres making up the layer 23, this embedded/integrated manner of the components 18,19 is distinct from different embodiments where the components 18,19 can be applied (e.g. stitched, adhered, etc.) overtop or underneath the layer 23 and as such are not considered as embedded/integrated and are instead considered as overlapping.

It is contemplated that the garment 10 can be worn by any person 12 including a female or male of small, medium, or large build. In one embodiment the wearer 12 of the garment 10 can be a yoga student 12 and/or yoga practitioner 12. In another embodiment the wearer 12 of the garment 10 can be a practitioner 12 or student 12 of Iyengar yoga.

Sensors 18

The sensor 12 can be any type of sensor 12 capable of attaching to fabric later 23 of a garment 12 in order to detect the movement and/or activity of a skin surface 14, muscle 14, and or muscle groups 14 of a wearer 12 of the garment 10. In one embodiment the sensor 18 can be a stretch sensor 18 knitted or otherwise woven as some of the plurality of fibres comprising the garment body layer 23. The stretch sensor 18 can be for example a capacitive and/or resistive sensor 18 which changes its capacitance or resistance as a function of elongation of the fibres comprising the stretch sensor 18. For example, the stretch sensor 18 can have a nominal resistance when relaxed and the resistance of the sensor 18 can gradually increase as the sensor 18 is stretched (i.e. the fibres composing the sensor 18 are stretched). It is recognised that the sensors when knitted or woven as part of the other fibres in the garment body layer 23 can include conductive only or both conductive and non-conductive fibres (e.g. threads).

The sensor 18 can be a stretch sensor 18 configured as a flexible cylindrical cord/fibres having electrical terminals at each end connected to the conducive pathway(s) 19 and/or the electrical connector(s) 21. In one embodiment the stretch sensor 18 can include an electroactive polymer (EAP) including a dielectric EAP (e.g. dielectric elastomer), ferro-electric EAP, electrostrictive graft polymer, and/or liquid crystalline polymer. The stretch sensor 18 can include other stretch-conductive materials such as rubber, nylon (e.g. silver-coated nylon), synthetic polymer, etc. In one aspect the stretch sensor 18 can be a circular-knit stretch sensor 18 incorporated as part of the other fibres in the garment body layer 23. In some embodiments, the stretch sensor 18 can include fabric (e.g. nylon) of the same type that is incorporated (e.g. knit) into other parts 22, 24 of the garment 10. In another aspect the stretch sensor 18 can include one or more materials (e.g. an electroactive polymer) that are only found on or in the garment 10 as part of the stretch sensor 18. In one embodiment the sensors 18 are strengthened with silicon.

The sensor 18 can be one or more conductive threads/fibres woven or knit into a pattern at specified locations of the garment 10 in the garment body layer 23 as part of the plurality of fibres thereof. The pattern of conductive threads (i.e. sensor 18) can form one or more circuits (e.g. bridge circuit) and electricity supplied to the pattern of conductive threads (e.g. from a power source attached to the suit) can be measured in the circuit to detect changes in capacitance and/or resistance of the thread pattern as the garment 10 fabric adjacent the conductive thread pattern is stretched. For example, the thread pattern (i.e. sensor 18) can be stretched along with the garment 10 as the garment wearer 12 tenses muscles 14 adjacent the garment 10 in the vicinity of the thread patterns 18. The pattern of conductive thread (i.e. sensor 18) can be any pattern and can include aesthetic aspects including one or more colours which are visible on the background colour(s) of fabric adjacent the conductive thread pattern 18.

The electrically conductive thread 18 incorporated into the garment 10 as one or more stretch sensors 18 can be made of any conductive material including conductive metals such as stainless steel, silver, aluminium, copper, etc. In one embodiment, the conductive thread can be insulated. In another embodiment, the conductive thread can be uninsulated. Typically the electrically conductive thread is inter-knit or woven with other textile-based threads (i.e. non-conductive or insulating) making up the body 23 of the garment 10. The other textile-based threads 18 making up the body 23 of the garment 10 can include any textile material such as cotton, spandex, nylon, polyester, and/or various synthetic materials. The electrically conductive thread 19 incorporated into the garment 10 as one or more conductive pathways 19 can be made of any conductive material including conductive metals such as stainless steel, silver, aluminium, copper, etc. In one embodiment, the conductive thread 19 can be insulated. In another embodiment, the conductive thread 19 can be uninsulated. Typically the electrically conductive thread 19 is inter-knit or woven with other textile-based threads (i.e. non-conductive or insulating) making up the body 23 of the garment 10. The other textile-based threads 19 making up the body 23 of the garment 10 can include any textile material such as cotton, spandex, nylon, polyester, and/or various synthetic materials.

Capacitance and/or resistance can be measured across all or a portion of conductive thread 18 and/or pattern of conductive thread 18. For example, changes in resistance and/or capacitance of the conductive thread 18 can be measured using a bridge circuit (e.g. a Wheatstone bridge or Wien bridge) contained or otherwise sensed by the controller device 16, a type, of electrical circuit in which two circuit branches are "bridged" by a third branch connected between the first two branches at some intermediate point along them. A source of power (e.g. a battery) of the controller device 16 can be connected to the bridge circuit along with a measuring device (e.g. a voltmeter, ammeter, or galvanometer) of the controller device 16 to detect changes in the resistance or capacitance of the conductive thread (i.e. sensor 18) as the thread changes length/width/thickness or other shape (e.g. due to stretching of the thread in response to tension in muscles 14 adjacent to the thread). Therefore the circuit can be calibrated to measure changes in length/width/thickness or other shape of the sensors 18 reflected as changes in the resistance and/or capacitance of the sensors 18.

It will be understood that the stretch sensor 18 (e.g. conductive thread) when attached/integrated to/into the fabric body layer 23 of a garment 10 can stretch when a skin surface 14 underlying the stretch sensor 10 moves and/or stretches (e.g. as a result of the activation of a muscle 14 or muscle group 14 controlling movement of the skin surface 14). Stretching of the stretch sensor 10 can result in generation of signals that can be communicated (e.g. via a cord or wires 19) to a receiving device 16 (e.g. an electronic device attached to the garment). For example, the stretch sensor 18 can be configured to generate an electric signal in response to stretching/elongation (i.e. the stretch sensor 18 can self-report on changes to its length). In another embodiment, an electric circuit (e.g. bridge circuit) can be attached to the stretch sensor 18 (e.g. conductive thread) for measuring changes in capacitance or resistance across the sensor 18 as the sensor changes in shape (i.e. an electric circuit can report on changes detected in resistance and/or capacitance of the stretch sensor 18). The electric circuit can include a measuring device (e.g. ammeter, voltmeter, galvanometer) which can measure changes in the resistance and/or capacitance of the stretch sensor 18 and report the measured changes to an electronic device 16 of the garment 10 for processing (e.g. via a processor of the device 16 and/or of the device 200).

The magnitude of the signal generated by the stretch sensor 18 can vary according to the amount of stretch induced in the stretch sensor 18 by movement of the underlying skin surface 14. Accordingly, a signal transmitted from the stretch sensor 18 (e.g. as a result of self-reporting of the stretch sensor 18 or reporting by a circuit attached to the stretch sensor 18) can carry information representative of whether a particular muscle 14 or muscle group 14 (i.e. controlling the movement of an underlying skin surface 14) is active as well as the degree or amount of the activity of the muscle 14 or muscle group 14. In one embodiment, the signal transmitted from the stretch sensor 18 represents the degree of stretching of the sensor 18 with a precision having an error of less than 1 mm. Further, signals transmitted from a stretch sensor 18 in response to movement of a skin surface 14 underlying the stretch sensor 18 can be monitored over time (e.g. by a processor of the device 16 receiving the signals) to derive a temporal pattern of activity of a particular muscle 14 or muscle group 14 which controls the movement of the skin surface 14.

In another embodiment, the sensor 18 is an EMG-sensor 18 that detects and/or measures muscle 14 activity.

Sensor 18 Attachment and Positioning

The sensor 18 (e.g. stretch sensor) can be incorporated into a garment 10 by embedding or encapsulating via knitting/weaving the sensor 10 into textile garment body layer 23 of the garment 10 represented by a plurality of threads/fibres knitted/woven as comprising the garment body layer 23. As such, the sensor 18 as well as the conductive pathway 19 are considered as part of the knitted/woven fibres comprising the garment body layer 23, such that removal of the component 18,19 fibres from the other fibres of the garment body layer 23 would compromise the structural integrity of the integrated plurality of fibres of the garment body layer 23. For example, a stretch sensor 18 can be stitched or sewed to/into the fabric layer 23 of the garment 10, either at the time of manufacture (i.e. integrated or embedded and therefore structurally integral with the other plurality of fibres of the garment body layer 23) or after manufacture (i.e. overlapping the layer 23 and therefor mot embedded or otherwise structurally integral with the other plurality of fibres of the garment body layer 23) of the garment 10. In one embodiment, a fabric pocket is stitched on an inner (i.e. normally skin-facing) periphery of the garment 10 to hold and protect the sensor 18. During manufacture of the garment 10 the sensor 18 can be inserted into the pocket and the pocket then enclosed (e.g. with stitching) to secure the sensor 18 within and thus only overlapping the garment body layer 23 (i.e. the sensor is a separate distinct layer from the garment body layer 23). Typically the pocket is sized to facilitate stretching of the sensor 18 in response to the stretching of an underlying skin surface 14. In another embodiment, conductive threads 18,19 can be woven/knitted into the fabric layer 23 of the garment 10 as a thread pattern. Changes in the length of the woven/knitted conductive thread pattern (i.e. sensor 18) can cause corresponding changes (detected for example by a voltmeter or ammeter operably connected to a bridge circuit of the device 16) in the resistance and/or capacitance of the woven/knitted pattern thereby giving an indication of the degree of stretch of the muscles 14 adjacent to the woven/knitted pattern 18.

Alternatively, the sensor 18 (e.g. stretch sensor) can be incorporated into a garment 10 by adhering the sensor 18 to a surface of the layer 23 of the garment 10. For example, a pre-manufactured standard yoga suit 10 can be retrofitted to include one or more sensors 18. For example, a stretch sensor 18 can be adhered to fabric layer 23 at an inner or outer surface of the yoga suit 10 by any of a variety of adhesive substances including tape and glue. In a further embodiment, a garment 10 can include an applied stretch sensor (e.g. stitched to fabric layer 23 of the garment 10 and thus overlapping the garment body layer 23 as a separate applied layer distinct from the garment body layer 23) and a stretch sensor 18 adhered (e.g. by an adhesive) to fabric at a surface of the garment. An example of an overlapping (and thus not embedded) sensor 18 is a topstitched series of conductive fibres on top of the plurality of fibres making up the garment body layer 23.

Typically when a garment 10 includes a stretch sensor 18 the stretch sensor 18 is integrated (e.g. embedded via interwoven or interknitted with other fibres comprising the garment body layer 23, applied as overlapping via stitching or adhesive, etc.) with the garment 10 such that the degree of stretch of the stretch sensor 18 closely approximates the degree of stretch of adjacent textile in response to a movement or stretch of a wearer 12 of the garment 10.

Herein when a garment 10 is described as having a particular "portion" 22,24 (e.g. "upper front thigh portion" or "back shoulder portion"), the adjectives preceding the word "portion" 22,24 (e.g. "upper front thigh" or "back shoulder") refer to the part of the body 14 which during normal use of the garment 10 underlie that portion 22,24 of the garment 10. Likewise, the directional terms "right" and "left" when used to describe a portion 22,24 of a garment (e.g. "right shoulder of a garment") refer to the particular lateral side of the body 14 occupied by that portion 22,24 of the garment 10 during regular use of the garment 10. Likewise the directional terms "front" and "back" when used to describe a portion 22,24 of a garment 10 (e.g. "back shoulder portion") indicate whether the portion 22,24 of the garment 10 occupies a position at the front or back of the body 14 when the garment 10 is worn.

A sensor (e.g. stretch sensor) 18 or group of sensors 18 on (e.g. overlapping) or in (embedded/integrated/integral) a garment 10 can be positioned anywhere within (embedded/integrated/integral) the garment 10 and/or across (e.g. overlapping) the surface of the garment 10. In one embodiment, the position of a sensor 18 attached/embedded to fabric 23 of the garment 10 corresponds (i.e. when the garment is worn) to the position of a skin surface 14 which can stretch during a yoga exercise. For example, a sensor 18 can be attached to fabric of a shoulder portion 24 of a form-fitting leotard 10 so that when the leotard 10 is worn the sensor 18 overlies a skin surface 14 of a corresponding shoulder 24 of the wearer 12 during a yoga exercise. In one embodiment, the sensor 18 can be positioned on or in the garment 10 (e.g. leotard) to overlie a skin surface 14 which stretches when a particular yoga exercise is performed correctly. In another embodiment, the sensor 18 can be positioned on or in the garment 10 (e.g. leotard) to overlie a skin surface 14 which stretches when a particular yoga exercise is performed incorrectly. In another example, a sensor 18 can be attached (e.g. by stitching or adhesion or otherwise embedded via weaving or knitting) to/in fabric layer 23 of a garment 10 such as a belt or band (e.g. arm-band) that can be form-fittingly wrapped or wound around a body portion 14 of a yoga student 12 to detect stretching of a skin surface 14 during a yoga exercise. The belt or band 10 can be applied form-fittingly around the body portion 14 such that the sensor 18 on or in the belt or band garment layer 23 is positioned over the skin surface 14 to be monitored for stretching. In one embodiment, application of the belt or band 10 to the body portion 14 positions the sensor 18 over a skin surface 14 which stretches when a particular yoga exercise is performed correctly. In another embodiment, application of the belt or band 10 to the body portion 14 positions the sensor 18 over a skin surface which stretches when a particular yoga exercise is performed incorrectly.

In one embodiment the garment 10 includes a first sensor 18 oriented longitudinally from a portion 24 of the garment 10 under the arms 14 to a hip portion 24, a second sensor 18 oriented longitudinally from a belly portion 24 to a thigh portion 24, a third sensor 18 on/in the back 24 of the garment 10 oriented laterally between opposed shoulder portions 24, a fourth sensor 18 on the back 24 of the garment 10 oriented laterally between opposed armpits 14, and a fifth sensor 18 on the back 24 of the garment 10 oriented laterally between opposed buttocks 14.

A sensor (e.g. stretch sensor) 18 can be attached to fabric layer 23 of a garment 10 in a longitudinal or lateral orientation. Herein the term "longitudinal" refers generally to the orientation of a sensor 18 of a garment 10 in a direction that is at least partially vertical (i.e. up-down) when the garment 10 is worn by a person 12 standing in an upright posture. Therefore, in general, the term "longitudinal" in reference to a garment 10 according to the embodiments corresponds to the proximodistal axis of a person 12 wearing the garment 10. For example, a sensor 18 which extends vertically along a garment (e.g. from a right shoulder portion 24 to a right hip portion 24 of the garment 10) when the garment 10 is worn by a person 12 standing in an upright posture is oriented longitudinally. In another example, a sensor 18 positioned on or in a garment 10 on a diagonal (e.g. from a left front shoulder portion 24 to a right buttock portion 24 of the garment 10) when the garment 10 is worn by a person standing in an upright posture can be oriented longitudinally. Herein the term "lateral" refers generally to the orientation of a sensor of a garment 10 in a direction that is at least partially horizontal (i.e. left-right) when the garment 10 is worn by a person standing in an upright posture. Therefore, in general, the term "lateral" in reference to a garment 10 according to the invention corresponds to the mediolateral axis of a person 12 wearing the garment 10. For example, a sensor 18 which extends horizontally across a garment 10 (e.g. from a right shoulder portion 24 to a left shoulder portion 24 of the garment) when the garment 10 is worn by a person 12 standing in an upright posture is oriented laterally. In another example, a sensor 18 positioned on or in a garment 10 on a diagonal (e.g. from a left front waist portion 24 to a right buttock portion 24 of the garment 10) when the garment 10 is worn by a person 12 standing in an upright posture can be oriented laterally. It will be understood that a particular orientation of a sensor 18 of a garment 10 can have both longitudinal and lateral aspects and that for this reason the terms "longitudinal" and "lateral" are not mutually exclusive herein. Generally, a sensor 18 extending diagonally across a garment 10 is referred to as longitudinally oriented (as opposed to laterally oriented) where the diagonal has a greater vertical component than horizontal component when the garment 10 is worn by a person 12 standing in an upright posture. Likewise, generally a sensor 18 extending diagonally across a garment 10 is referred to as laterally oriented (as opposed to longitudinally oriented) where the diagonal has a greater horizontal component than vertical component when the garment 10 is worn by a person 12 standing in an upright posture. It will be recognized that in some cases (e.g. where the vertical and horizontal components of a diagonal sensor 18 are approximately the same) a sensor 18 can be referred to as either laterally or longitudinally oriented. Further, different portions of a single sensor 18 (e.g. stretch sensor) of a garment 10 can assume different orientations (e.g. longitudinal and lateral) due to attachment/integration of the sensor 18 to the garment 10 in a bent or curved configuration.

Garment 10 Functionality

The garment 10 can be form-fitting to facilitate stretching of the fabric 23 and sensors 18 (e.g. stretch sensors) of the garment in response to the movement and/or stretching of a skin surface 14 underlying the garment. In effect the garment can be a "second skin" that replicates or simulates or follows movement of the underlying skin surface, for example during a yoga exercise. In one aspect, the garment can replicate or simulate the movement of the skin surface by moving in response to and as a result of the movement of the underlying skin surface, in another aspect, the garment can replicate or simulate the movement of the skin surface by moving in the same direction or pattern as the underlying skin surface. For example, stretching/movement of the skin surface in an upward direction by a yoga student 12 to effect a yoga posture can induce stretching/movement of the overlying garment fabric and sensors in an upward direction, whereas release of the posture by the yoga student to move the skin surface downwards can induce downward movement of the overlying garment fabric and sensors. In another aspect, the garment can replicate or simulate the movement of the skin surface by moving the same amount or extent as the underlying skin surface during a yoga exercise. For example, during an exercise a yoga student can hold a slight stretch for a period of time and then extend the slight stretch into a full stretch. The fabric and sensors of the garment can be induced by execution of the slight stretch to move/stretch approximately the same amount as the movement/stretching of the underlying skin surface during the slight stretch, and then be induced by execution of the full stretch to move/stretch a further amount that closely corresponds to the movement/stretching of the underlying skin surface during the full stretch. It is recognised that the conductive pathways 19 can be correlated to also stretch with movement and thus also change in their resistive/capacitive characteristics within the overall electronic circuit comprising the controller 16 (e.g. with power source), connector 21, conductive pathway(s) 21 and the sensor(s) 18. Alternatively, the conductive pathways 19 can be correlated to also inhibit stretching with movement and thus to remain relatively constant (or otherwise considered minimally to change within a defined delta band) in their resistive/capacitive characteristics within the overall electronic circuit comprising the controller 16 (e.g. with power source), connector 21, conductive pathway(s) 21 and the sensor(s) 18.

Therefore a form-fitting garment 10 according to the embodiments can include a sensor which when the garment is worn is positioned adjacent to a skin surface of the wearer without being affixed to the skin surface, in contrast to affixing (e.g. using adhesive tape) a sensor directly to a skin surface to detect movement. The affixing of a sensor (e.g. stretch sensor) directly to a skin surface can obstruct the movement (e.g. stretching) of the affixed sensor in response to movement of the skin, whereas a sensor of a garment according to the embodiments can be free to move (e.g. stretch) with the movements of the skin (i.e. in response to skin movement and in the same direction as the skin movement and to the same extent as the skin movement).

In an embodiment, a garment 10 can include a single stretch sensor to detect stretching of a skin surface in response to activity of a particular muscle or muscle group during a yoga exercise. For example, a sensor 18 can be laterally oriented at a back 24 of a garment between right and left shoulder portions 24 of the garment to monitor (i.e. via the stretching of a skin surface 14 underlying the sensor 18 when the garment is worn) the activity of muscles located in the upper torso 14. In another example, the activity of muscles located in the upper torso 14 can be monitored by a sensor extended across a chest portion 24 of a garment from a back right shoulder portion 24 of the garment to a back left shoulder portion 24 of the garment.

In another embodiment, a garment 10 can include multiple stretch sensors 18 attached/embedded/embedded to fabric 23 of the garment at different positions 24 to detect stretching of multiple skin surfaces 14 in response to activity of one or more muscles or muscle groups 14 during a yoga exercise. For example, first and second sensors can each be attached/integrated/embedded longitudinally to fabric 23 positioned at opposing side peripheries of a garment from a respective upper hip portion 24 of the garment to a respective armpit portion 24 of the garment to monitor activity of muscles groups 14 located on opposing side peripheries of the torso 14. In another example, a garment can include a first sensor in a lateral orientation between an upper front thigh portion 24 of the garment to a navel portion 24 of the garment and a second sensor in a lateral orientation between opposing buttock portions 24 of the garment, in order to monitor activity of muscles 14 located in the hips 14 and pelvis 14 of a wearer 12 of the garment 10. In one embodiment, the second sensor extending laterally between opposing buttock portions 24 can be approximately 6 cm long.

Therefore a sensor 18 (e.g. stretch sensor) of a garment can be attached/integrated/embedded to/into fabric 23 of the garment 10 at a specific position to detect and/or measure movements of a particular skin surface underlying the sensor induced in response to the activity of muscles used during a yoga exercise performed by a yoga student wearing the garment. For example, one or more sensors of the garment can measure alignment of a part of the body 14, stretching (e.g. at the sides of the body), lifting of a part of the body (e.g. pelvis or shoulder blades), and activation of muscles central to core alignment in yoga (e.g. via detection of skin movements induced in response to the muscle activity). In one embodiment, a garment includes a stretch sensor on a chest portion 24 of the garment to generate signals representative of breathing frequency of a wearer of the garment.

In an embodiment, a stretch sensor attached to/into fabric 23 of a garment stretches in response to movement of a skin surface (e.g. during a yoga posture of a student) underlying the sensor thereby generating a signal that can be transmitted by the sensor to an electronic device 16 of the garment attached to fabric 23 of the garment. Alternatively, a measuring device 16 (e.g. voltmeter ammeter, and/or galvanometer) can be attached to the sensor (e.g. conductive thread) and can detect changes in sensor shape by applying power through an electric circuit (e.g. a bridge circuit as part of the conductive pathway(s) 19) attached between the sensor 18 and the measuring device 16 via the connector(s) 21. A processor of the device 16 receiving the signal (e.g. from the electronic device of the garment) can assess the signal to determine whether or not a particular muscle group known to move the skin surface underlying the sensor is active (e.g. during the yoga exercise). Because the signal generated and transmitted by the stretch sensor to the processor (e.g. via the electronic device 16) can include information (e.g. as signal magnitude) representative of the amount of stretching of the stretch sensor, which directly corresponds to the amount of stretching of the underlying skin surface, the processor can further determine an approximate amount of activation of the muscle group. Further, a processor can monitor signals received from the stretch sensor over time (e.g. during the yoga posture) to determine the temporal pattern of activation of the muscle group controlling movement of skin underlying the stretch sensor. The processor can integrate signals received from multiple stretch sensors of a garment during a yoga posture to map which muscles are being used/activated during the posture as well as the degree of use/activation of each muscle at a specific moment during the exercise and/or over time, based upon the particular portions 24 of the sensors 18 (as compared to the portions 22 in which no sensors are located) as known to the computing device 16,200. By comparing the pattern of activity (i.e. spatial and/or temporal) of a grouping of muscles during a yoga posture to a standard pattern of activity (e.g. representing an ideal or correct pattern of muscle activity during that yoga exercise) stored in memory accessible to the processor, the processor can generate feedback for viewing by a student reporting the results of a yoga posture and/or coach a yoga student towards improving the posture in the future. Therefore, the present disclosure provides a system for a yoga student to self-monitor the success of performing a particular yoga posture and to track progress in the performance of the posture over time.

Electronic Device 16 and Power Source

The garment 10 can include an electronic device 16 connected to fabric 23 of the garment and/or secured to the garment for receiving signals indicative of changes in the stretching of a portion 24 of the garment. For example, the electronic device can receive signals generated and transmitted by one or more stretch sensors 18 of the garment. In another embodiment the electronic device can receive signals from a measuring device (e.g. voltmeter ammeter, galvanometer) attached to the sensor that detects changes in sensor shape when power is applied to the sensor through an electric circuit (e.g. a bridge circuit or other conductive pathways 19) attached between the sensor 18 and the measuring device 16. The electronic device typically includes a transmitter (e.g. wireless transmitter) for transmitting signals received from a sensor to a computing device 200 (e.g. a mobile computing device of a yoga student wearing the garment). The electronic device 16 can be any device capable of being incorporated into a garment for receiving signals from one or more sensors of the garment and transmitting the received signals (e.g. via a wireless transmitter) to a computing device 200. Non-limiting examples of an electronic device 16 according to the embodiments are a printed circuit board. RF module, transceiver module, and system-on-a-chip module. In one embodiment, the electronic device 16 can be an eight-channel printed circuit board having a Bluetooth low-energy wireless transmitter for transmitting the information received from a sensor 18 of the garment 10 to a computing device 200.

The electronic device 16 can exhibit exact (e.g. 1 ms or better) time-coding of sensor data received from the stretch sensors of the garment. In one embodiment, the electronic device can include a processor for processing signals received by the electronic device from one or more sensors (e.g. stretch sensors) of the garment. In a further embodiment, the electronic device can include a gyroscope, accelerometer, and/or magnetoscope for generating data pertaining to the orientation of the electronic device of the garment. The electronic device can generate orientation data to augment the information received from one or more sensors of the garment, and for example transmit the orientation data together with the sensor data wirelessly to a receiving computing device 200.

The electronic device 16 can be secured to fabric 23 of the garment for example by stitching or by an adhesive. For example, the electronic device can be attached to a first fabric 23 (e.g. adhered to the periphery of the electronic device) that can be stitched to a second fabric of the garment at a surface of the garment to secure the electronic device at a periphery of the garment. Alternatively, a pocket can be stitched into a periphery of the garment (e.g. at an inner surface of the garment) for receiving the electronic device. The pocket can be configured to open and close (e.g. using Velcro pads) to facilitate the removal of an electronic device received by the pocket (e.g. to facilitate washing of the garment). In another example, the electronic device can be adhered to a surface of the garment using an adhesive such as glue or tape.

The electronic device can be secured to fabric of the garment positioned at any portion of the garment. In one embodiment, the electronic device can be secured to fabric at a position where the electronic device has a minimum influence on a yoga student's ability to move during a yoga exercise. For example, the electronic device can be positioned immediately below a shoulder portion of the garment.

It will be recognized that a sensor 18 (e.g. stretch sensor) of a garment can communicate with an electronic device 16 of the garment in a variety of ways. For example, signals generated by the sensor can be transmitted to the electronic device via a flexible wire or cord (e.g. conductive pathway 19 comprising one or more conductive/non-conductive fibres) attached to the layer 23 (e.g. overlapping) or otherwise embedded/integrated (e.g. knit/woven) along with as part of the plurality of fibres making up the garment body layer 23. Typically where signals are communicated between the stretch sensor and electronic device via a wire or cord 19, the wire or cord 19 is incorporated into the garment 10 in a way that preserves flexibility (e.g. stretching) of the garment and does not constitute a significant obstacle to the execution of yoga positions by a wearer of the garment. In one embodiment, the wire or cord 19 can include a stretchable (e.g. elastic) material (e.g. conductive fabric) capable of stretching in response to the movement of a skin surface underlying the wire. In another embodiment, the wire or cord can be positioned on/in extreme lateral portions 22,24 of the garment, and the wire or cord 19 can cross a front or back of the garment as required to connect to the electronic device 16 and one or more sensors 18 of the garment. The wiring 19 can be made in a stretchable pattern and can be applied to/in the fabric 23 of the garment 10 in different aesthetic inspirations including a meander bandpattern. The wiring 19 can also assume different colours or colour combinations depending on the colour or colours of the garment. It is contemplated that the wire 19 can be a conductive thread or threads composed at least partially of silver or stainless steel (or other conductive materials).

A power source of the controller 16, for example, can be attached via the connector(s) 21 to the garment body layer 23 for providing power to one or more sensors 18 and an electronic device 16 attached to the garment 10. In one embodiment, the power source can be a battery included within the electronic device. The power source can be actuated for example by an on-off switch connected to the power source and accessible to a wearer of the garment.

Application 201

The system can include an application 201 running on a computing device 200 (e.g. smartphone or tablet) that can receive a transmission from the electronic device of the garment including sensor data representative of information received by the electronic device 16 from one or more sensors 18 (e.g. stretch sensors) of the garment 10 and optionally orientation data generated by the electronic device 16. The data (e.g. sensor data and/or orientation data) received by the computing device 200 from the electronic device 16 can be stored by the computing device 200 in memory accessible by a processor of the computing device 200 capable of running the application 201.

The application 201 can be programmed to instruct the processor to parse and/or interpret the sensor data received from the electronic device of the garment. For example, where a garment includes a plurality of sensors, the application can parse the sensor data into separate pools of data where each pool contains data collected by a different sensor during an activity (e.g as a yoga exercise) involving movement of one or more body portions 14 underlying the sensor(s) 18 on/in the layer 23 of the suit portion 24 adjacent to the one or more body portions 23. The processor can interpret the data from each pool to determine the pattern of activity of a single sensor throughout the duration of the (yoga) exercise. For example, the application can determine whether or not a particular sensor was active (i.e. transmitted a signal to the electronic device) during the exercise and when during the exercise the sensor was active. If the processor determines that a particular sensor was active (i.e. transmitted a signal to the electronic device) at a particular time during the exercise, then the processor can further determine the magnitude of the signal generated by the sensor at that time (e.g. for a stretch sensor, the magnitude of the signal can vary as a function of the elongation/stretch/change of shape of the sensor).

It will be recognized that for a given (yoga) exercise performed by a (yoga) student 12 the application can process the sensor data to derive one or more sensor activity maps specific to each sensor of the garment. Each sensor activity map can represent the temporal pattern of signal generation of a specific sensor including the magnitude of each signal generated by the sensor. Where a garment includes multiple sensors, the application can further process the sensor data to derive a garment activity map representative of the temporal and spatial pattern of activity of the plurality of sensors attached to fabric of the garment. For example, the application can process the sensor data to determine that during the first 30 seconds of a particular yoga exercise a first sensor positioned on a right shoulder portion of the garment generated a signal at 25% magnitude, a second sensor positioned on a left shoulder portion of the garment generated a signal at 50% magnitude, and a third sensor located on a right hip portion of the garment did not generate a signal.

The application can be programmed to access body data stored in a memory of the computer device. The body data can instruct the application regarding the association between activity of a particular sensor and the relative position of the sensor over the body of a yoga student. For example, the body data can instruct the processor that a first sensor generating a first signal represented in the sensor data is positioned on a left shoulder portion of the garment and a second sensor generating a second signal represented in the sensor data is positioned on a right shoulder portion of the garment. The body data can additionally include information pertaining to the identity of muscles or muscle groups which control the movement or stretching of a skin surface underlying a particular sensor. For example, the body data can instruct the application that a first sensor positioned on a left shoulder portion of the garment typically detects movement controlled by a left deltoid muscle. Further, the body data can include representations of the correlation between a particular magnitude of a sensor signal represented in the sensor data and the degree of activity of a muscle controlling a skin surface underlying the sensor. For example, the body data can instruct the application that a 50% magnitude of a signal represented in the sensor data corresponds to 50% activation of the muscle controlling movement of the skin surface underlying the sensor.

As will be understood, the application can process the sensor data in conjunction with the body data to derive a body activity map during a particular yoga exercise. The body activity map can represent the temporal and spatial pattern of muscle activity of a yoga student during the execution of a yoga posture. For example, the application can process the sensor data in conjunction with the body data to derive a body activity map representing that during the first 30 seconds of a yoga posture a left deltoid muscle of a student wearing a garment according to the invention was 100% more active than a right deltoid muscle of the student and that a right gluteal muscle was not active. In another example, a body activity map can represent that during a first 30 seconds of a yoga posture dorsal muscles located in the back of the student were active and frontal muscles located in the front of the student were inactive, while during the second 30 seconds of the yoga exercise the frontal muscles were active and the dorsal muscles were inactive.

The sensor map, garment map, and/or body activity map can be displayed by the application on a user interface of the computing device for viewing by for example a yoga student who was the source of the sensor data by wearing a garment according to the invention during a yoga posture. For example, the computing device can display on a user interface a body activity map generated by the processor from sensor data collected during a yoga posture performed by a yoga student. The student can view the body activity map to assess which muscles were active during the posture, the degree of activity of each active muscle, and the timing of activation of each muscle during the posture.

A memory of the computing device can store a standard activity map for a given yoga exercise representative of an ideal or "correct" pattern of sensor activation and/or muscle activity during the exercise. The application can compare one or more of the sensor activity map, garment activity map and body activity map to the standard activity map to determine whether and how the maps differ. For example, a standard activity map can indicate that during a particular yoga exercise a left deltoid muscle and a right deltoid muscle are each 30% active for the first 30 seconds of the exercise, while a right gluteal muscle is 20% active. The processor can generate a body activity map from the sensor data in conjunction with the body data representing that for the first 30 seconds of the exercise a right deltoid muscle was active at 25%, a left deltoid muscle was active at 50%, and a right gluteal muscle was not active. The application can compare the body activity map to the standard activity map to determine that the body activity map differs from the standard activity map in that the right deltoid muscle was 5% underactive, the left deltoid muscle was 20% overactive, and the right gluteal muscle was inactive when it should have been active at 20%.

The computing device can display the results of a comparison of a map generated from the sensor data (e.g. body activity map) to a standard activity map on a user interface of the computing device for viewing by a user of the computing device (e.g. a yoga student who was the source of the sensor data by wearing a garment according to the invention). Accordingly, a yoga student who executed a particular yoga exercise can assess whether and how the pattern of muscle activity (e.g. spatial and/or temporal) in the body of the student during the yoga exercise differs from an ideal standard pattern of muscle activity. In one embodiment, the application can highlight on the display (e.g. through words or pictures) how the student's performance of the exercise differs from the standard. The application can also include a "coaching" function which provides tips for a yoga student for future performance of an exercise based on the results of the processing of the sensor data. For example, the application can coach the student that in the future for the posture held for the first 30 seconds of the exercise the student should flex the right side of the body including the gluteal and deltoid muscles while relaxing the left side of the body including the left deltoid muscle. In another embodiment, the application can determine that one or more muscles were improperly active at a time during a yoga exercise when it should not have been active. In such a case the results of the processing displayed by the application on a user interface of the computing device to a student can highlight that the muscle was improperly activated, and coach the student to relax the muscle during the yoga exercise in the future.

In one embodiment, an exercise (e.g. dance exercise) can be performed by a student to a soundtrack (e.g. music) having a particular temporal rhythm of beats which can be stored in a memory of the computing device. The application can access the stored temporal rhythm of beats to compare the timing of the beats in the soundtrack played during the exercise to the temporal activity of one or more sensors and/or muscles during the exercise. In one embodiment, the memory of the computing device can store a standard activity map as an ideal or "correct" pattern of muscle activity during an exercise performed while the soundtrack is playing. For example, the standard activity map can represent that particular muscles should be activated "on the beat" of the temporal rhythm of beats of the soundtrack. The application can compare the standard activity map corresponding to the temporal rhythm of beats of the soundtrack to a body activity map generated from sensor data received from a garment worn by a student to determine whether and how the pattern of muscle activity of the student differ from the ideal pattern of muscle activity represented by the standard activity map. The computing device can display the results of the comparison on a user interface of the device to for example the student, and where the body activity map differs from the standard activity map, can additionally coach the student regarding how to improve future performance of the exercise.

The application can store the results of processing of sensor data received from a garment during one or more yoga exercises. The application can be configured to compare results of different performances of the same yoga exercise to assess the progress of for example a yoga student's performance of the exercise over time. For example, the application can compare the results of first and second body activity map/standard activity map comparisons conducted using sensor data received by the application from the garment during performances of an exercise conducted one week apart. The application can display the results of the comparison on a user interface of the computing device for viewing by the student in order for the student to assess whether or how the second performance is an improvement over the first performance (e.g. the body activity map of the second performance more closely resembles the standard activity map than the body activity map of the first performance thus indicating an improvement in performance by the student over time). In another embodiment the application can rank performances (e.g. of a particular yoga posture) by the correctness of the posture relative to a standard activity map.

Therefore, in one embodiment the application can include an interaction mode which provides visual feedback to a yoga student by displaying the results of the processing of sensor data to the student for retrospective evaluation (e.g. after-class evaluation) of the performance of a yoga exercise (e.g. yoga posture). In an embodiment where the sensor data is collected by the application from a garment worn by a student during a yoga class, at the beginning of the class the student can turn on the yoga application and the power source of the garment for supplying power to the sensors and the electronic device of the garment. The student can then proceed to perform one or more yoga postures while wearing the garment. During performance of the yoga postures the sensors (e.g. stretch sensors) connected to the fabric of the garment can generate signals in response to movement of a skin surface underlying the sensors and transmit the generated signals via a cord or wire to the electronic device. The electronic device can include a network module (e.g. Bluetooth capability) that transmits the information received from one or more sensors of the garment as sensor data to a computing device (e.g. smartphone) running the yoga application. The yoga application can process the data received from the electronic device (e.g. in real-time) as described above. For example, the application can process the sensor data to generate a sensor map, a garment map, and/or a body activity map. Once the class is over the student wearing the garment during class can use the application to visualize the results of processing of the sensor data. For example, the student can view the results of a comparison of a body activity map generated by the application using sensor data received during the yoga exercise to a standard activity map stored in memory of the computing device. Alternatively the student can view comparisons of the results of the yoga postures just completed to results of the same yoga postures completed at an earlier time and/or to the student's best past performance of a particular posture as ranked by the application.

In another embodiment, the application can include a "real-time" interaction mode (e.g. a "teacher-assistant mode") by which the application can guide (e.g. with sound) a yoga student on the correct way to perform an exercise while the student is conducting yoga postures wearing a garment according to the invention. In one embodiment, the application provides feedback (e.g. audible feedback) to a yoga student regarding the performance of a yoga posture by the student. For example, in one embodiment the application can recognize a posture performed by a student by analyzing the quality of the sensor data received by the application (e.g. via a calibration of the application which corresponds a particular quality of sensor data to a particular yoga posture; see below). The application can then access a standard activity map corresponding to the posture stored by the computing device and use the information of the standard activity map to provide real-time audible feedback to the student based on the quality of the sensor data received by the application.

In another embodiment the student can instruct the application via the user display of the specific posture or exercise which is being performed. For a posture requiring tension of the shoulder muscles, the application can for example read the standard activity map to determine that right and left deltoid muscles of the student should be activated at approximately 50% during a first posture of the exercise. The application can then instruct the student in real-time (e.g. by sound via a speaker if the computing device) to flex left and right deltoid muscles to execute the posture. The application can receive sensor data in response to the student flexing the deltoid muscles which can be processed by the application to determine the degree of flexing of each deltoid muscle (e.g. as a result of calibration of the application; see below). The application can compare the determined degree of flexing of each deltoid muscle to the ideal or correct activity of the muscle obtained from the standard activity map and provide feedback to the student accordingly. For example, if the processor determines from the sensor data that the left deltoid muscle is activated at 75%, which is 25% more than the activity specified in the standard activity map, then the application can instruct the student (e.g. by sound) to relax the left deltoid muscle slightly. Relaxation of the left deltoid muscle by the student can then be reflected in the sensor data received by the application which can be interpreted by the application to determine whether as a result of the relaxation the posture is now being performed correctly. If the posture is being performed correctly (i.e. both the deltoid muscles are at or close to 50% activity) then the application can provide feedback to the student accordingly.

In another example, if the application detects via the received sensor data the activity of a muscle which the standard activity map indicates should not be active during a posture, then the application can provide real-time feedback to the student (e.g. by sound) to relax the muscle which is incorrectly flexed.

In some embodiments the application can provide real-time instructions or feedback (e.g. audible instructions or feedback via a speaker of the computing device) to a student that can be more detailed than whether to flex or relax a muscle. For example, the application can instruct the student to "stretch the sides of the body and hook the side ribs like the claws of a tiger", if the yoga student is entering the pose Sirsasana (head balance).

In a further embodiment the feedback communicated by the application to the student can be tactile feedback. For example, one or more vibratory devices can be attached to fabric of the garment at one or more specific garment portions (e.g. a shoulder portion) such that the device can vibrate in response to receiving a signal (e.g. from the electronic device of the garment). The signal can be transmitted to the vibratory device by the electronic device in response to a communication transmitted by the yoga application to the electronic device as feedback to the student in response to the quality of sensor data received by the application and processed by the application, for example by comparing the sensor data to standard activity data for a given yoga posture stored in the memory of the computing device. In one embodiment, the application compares sensor data received from the garment while the wearer of the garment is performing a particular posture to a standard activity map for the posture and detects a muscle (e.g. a left deltoid muscle) of the wearer which is under-activated. In response the application can transmit (e.g. wirelessly) information to the electronic device which induces the electronic device to send a signal to a vibratory device overlying a skin surface controlled by the under-activated muscle (e.g. left deltoid muscle) which in turn induces vibration of the vibratory device. Vibration of the vibratory device can act as feedback to the wearer of the garment to flex the under-activated muscle. In another embodiment, the application sends a communication (i.e. feedback) to the garment which induces a vibratory device to vibrate when the application determines that the muscle activity controlling a skin surface underlying the vibratory device is correct.

Therefore the system described herein can include grouping of sensors (e.g. pairings of sensors) attached to fabric of a garment for measuring activity of a plurality of muscles (e.g. via the movement of a skin surface controlled by the muscle) in order to improve a posture (e.g. yoga posture) of a person over time by providing feedback (e.g. visual, audible or tactile) to the person indicating specific actions to take to correct a defective aspect of the posture.

In one embodiment, the application can display the orientation data received from the electronic device on a user interface of the display.

The application (e.g. yoga application) can include a set-up or calibration mode in which the application can prompt a user to input data that the application can use to configure processing of sensor data. In one embodiment, the application can be programmable (e.g. by a user of the application) in the set-up mode to instruct the application regarding a particular configuration of the garment. For example, the application can be programmed with the particular positions of one or more sensors of the garment worn by person during an exercise. The application can display front and back depictions of a body on a user interface and prompt a user of the device to select (e.g. on a touch-screen display, by touching portions of the front and back depictions of the body) the portions of the body over which a sensor (e.g. stretch sensor) is positioned when the garment is worn. In another example, the application can be programmable in the set-up mode to indicate the ideal or "correct" correspondence between a particular temporal rhythm of beats of a soundtrack and muscle activity of a person performing an exercise while the soundtrack is playing.

In a further embodiment, the application can include a calibration feature which can enable a user of the garment (e.g. a yoga student) to instruct the application regarding the correspondence between activation of a particular muscle group and the quality of sensor data received by the application. For example, a person (e.g. yoga student) can wear the garment in the calibration mode and be prompted by the application (e.g. through a user interface of a mobile device running the application) to flex a particular muscle which controls movement of a skin surface underlying a particular sensor of the garment. The application can receive sensor data from the garment (i.e. via the electronic device) in response to activation of the muscle and thereby calibrate itself regarding the correspondence between the quality of sensor data received and the identity of a particular activated muscle group. In another example, the application can prompt a wearer of the garment to flex a particular muscle to different degrees (e.g. slightly, a moderate amount, as much as possible, etc.) in order for the application to instruct itself regarding the correspondence between the quality of sensor data received by the application and the degree of muscle activity. In another example, the calibration mode can be used for the application to instruct itself regarding a baseline level of muscle activity (i.e. muscle activity that exists due to inherent tension in the muscles in the absence of a wearer of the garment volitionally flexing a muscle) in a wearer of the garment.

In a further embodiment, the application can include a calibration mode which instructs the application regarding the correlation between the quality of sensor data received by the application and the performance of a particular yoga posture. For example, a student can be prompted in the calibration mode via a user interface of the computing device to perform a particular yoga posture while wearing the garment. The application can receive sensor data from the garment (i.e. via the electronic device) in response to the student's attempt at performing the posture and correspond the particular quality of the sensor data received to the posture performed thereby calibrating itself to recognize the student performing the posture by the quality of the sensor data received.

In an embodiment the system include a sensor device configured to process stretch data for determining a stretch value of a body part, where the sensor device comprises a stretch sensor directly connected to the body part for obtaining stretch data, where the stretch sensor is a capacitive or resistive sensor, which changes its capacitance or resistance as a function of elongation, where the sensor device is configured to process stretch data for the stretch sensor for determining a stretch value of the body part, where the sensor device comprises a processor configured for: analyzing the stretch data while the body part is in motion; analyzing the stretch data to identify portions of the cyclic stretch data which correspond to motions of the body part, where the portions of the stretch data are identified so that the portions contain first and second stretch data points associated with respective first and second motion-phases of the body part; analyzing the cyclic stretch data to identify first and second stretch values by determining minimum and maximum sensor values; further analyzing the cyclic stretch data to identify the portions ensuring that the portions contain portions of an entire period of a cyclic harmonic signal containing first and second stretch data points associated with respective first and second motion-phases of the body part and to distinguish values related to other motions phases: analyzing the identified portions of stretch data to determine first and second sensor values of the respective first and second stretch data points; and determining strength values by determining the differences between the first and second sensor values.

The application can be executed as a set of instructions by a processor of the computing device. Each of the modes (e.g. interaction mode; calibration mode) can also include a set of instructions for execution by the processor, and the processor can communicate with each of the modes and/or components of the modes to execute the instructions. For example, in the "real-time" interaction mode the processor can communicate with a speaker of the computing device to emit audible information to a wearer of the garment instructing the wearer to take a particular action (e.g. flex a left shoulder muscle). Therefore, it will be understood that the application includes executable instructions capable of receiving sensor data (and optionally orientation data), processing the received data, and displaying the results of the processing to a user interface of the computing device for display to a user of the computing device.

In view of the above, it is recognised that the application 201 can be configured as a general activity (e.g. yoga) based application 201 that is for monitoring the movement of the specified body portions 14 associated with the sensor(s) 18 in/on the garment fabric layer 23 adjacent to the body portion(s) 14.

Figure 9:
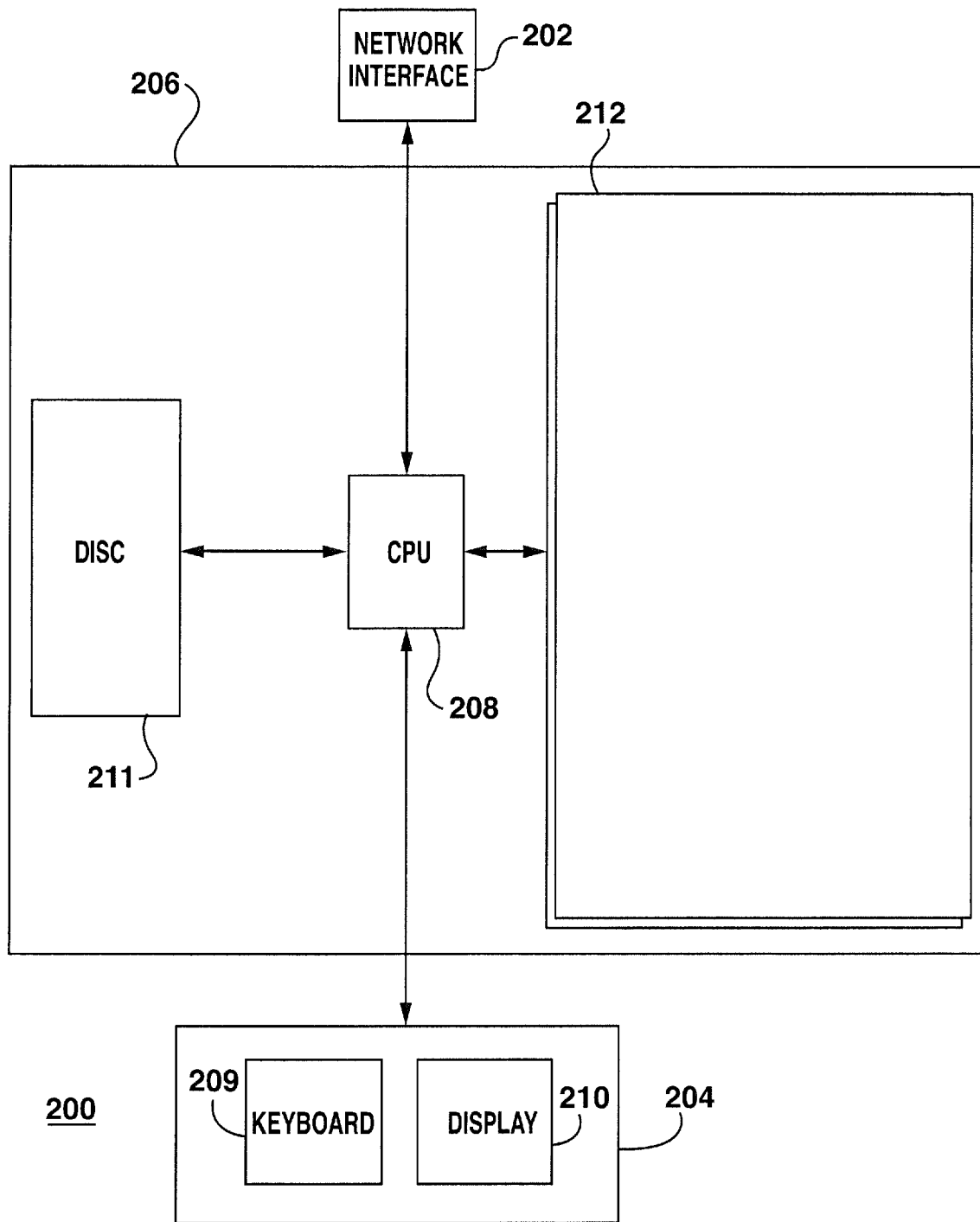
FIG. 9 is a block diagram of the communication device of FIG. 1.

Referring to FIG. 9, the computing device can be device 200. In some embodiments, the electronic device can be device 200. When electronic device is device 200, at least some of the sensor signal processing (and optionally the orientation data processing) can be done using the electronic device of the garment before sending the processed information (e.g. as sensor data) to the computing device.

The device 200 is configured to communicate over a communications network (e.g. Bluetooth, wireless network, etc.) with the connection interface 202. The application can receive data entry by the user (e.g. via the user interface 204) and/or by another application running on the data processing system 206 for accessing the sensor data (e.g. processed or otherwise).

The device 200 can be a land-based network-enabled personal computer. However, the invention is not limited for use with personal computers. For instance, the device 200 can comprise a wireless communications device, such as a wireless-enabled personal data assistant, a tablet, or mobile telephone if the communications network is configured to facilitate wireless data communication. In addition, the invention is not limited to only facilitating transmission of sensor data (and optionally orientation data) between the electronic device and computing device (e.g. device 200), and can be used to transmit raw data, processed sensor data, and/or any other multimedia data in addition or substitution of the sensor data, as desired.

A device 200 can comprise a network interface 202, a user interface 204, and a data processing system 206 in communication with the network interface 202 and the user interface 204. Typically, the network interface 202 comprises an Ethernet network circuit card, however the network interface 202 may also comprise an RF antenna for wireless communication over the communications network.

Preferably, the user interface 204 comprises a data entry device (such as keyboard 209, microphone or writing tablet), and a display device 210 (such as a CRT or LCD display). The user interface 204 can include one or more user input devices such as but not limited to a QWERTY keyboard (e.g. keyboard 209, a keypad, a stylus, a mouse, a microphone and the user output device such as an LCD screen display and/or a speaker. If the screen is touch sensitive, then the display can also be used as the user input device as controlled by the data processing system 206.

The device 200 can include a network interface 202, such as a network interface card or a modem, coupled via connection to a data processing system 206. The network interface 202 is connectable during operation of the device 200 to the network (e.g. an Intranet and/or an extranet such as the Internet), which enables the device 200 to communicate with each other as appropriate. The network can support the communication of the network messages for the various transmitted data (e.g. sensor data) there between.

The data processing system 206 can include a processor 208, and a non-volatile memory storage device (DISC) 211 (such as a magnetic disc memory or electronic memory) and a read/write memory (RAM) 212 both in communication with the processor 208. The DISC 211 includes data which, when loaded into the memory 212, comprise processor instructions for the processor 208 which define memory objects for allowing the device 200 to communicate over the communications network.

Operation of the device 200 is facilitated by the data processing system 206. The memory 212 is used to store data for access by the respective user and/or operating system/executable instructions of the device 2002. The processor 208 facilitates performance of the device 200 configured for the intended task through operation of the network interface 202, the user interface 204 and other application programs/hardware of the device 200 by executing task related instructions. These task related instructions can be provided by an operating system, and/or software applications located in the memory 212, and/or by operability that is configured into the electronic/digital circuitry of the processor(s) 208 designed to perform the specific task(s). Further, it is recognized that the data processing system 206 can include a computer readable storage medium 211 coupled to the processor 208 for providing instructions to the processor 208 and/or to load/update the instructions. The computer readable medium 211 can include hardware and/or software such as, by way of example only, magnetic disks, magnetic tape, optically readable medium such as CD/DVD ROMS, and memory cards. In each case, the computer readable medium 211 may take the form of a small disk, floppy diskette, cassette, hard disk drive, solid-state memory card, or RAM provided in the memory 212. It should be noted that the above listed example computer readable mediums 211 can be used either alone or in combination.

Further, it is recognized that the device 200 can include the executable applications comprising code or machine readable instructions for implementing predetermined functions/operations including those of an operating system. The processor 208 as used herein is a configured device and/or set of machine-readable instructions for performing operations as described by example above. As used herein, the processor 208 may comprise any one or combination of, hardware, firmware, and/or software. The processor 208 acts upon information by manipulating, analyzing, modifying, converting or transmitting information for use by an executable procedure or an information device, and/or by routing the information with respect to an output device. The processor 208 may use or comprise the capabilities of a controller or microprocessor, for example. Accordingly, any of the functionality of the executable instructions (e.g. through modules associated with selected tasks) may be implemented in hardware, software or a combination of both. Accordingly, the use of a processor 208 as a device and/or as a set of machine-readable instructions is hereafter referred to generically as a processor/module for sake of simplicity. The memory 212 is used to store data locally as well as to facilitate access to remote data stored on other devices connected to the network.

The data can be stored in a table, which can be generically referred to as a physical/logical representation of a data structure for providing a specialized format for organizing and storing the data. General data structure types can include types such as but not limited to an array, a file, a record, a table, a tree, and so on. In general, any data structure is designed to organize data to suit a specific purpose so that the data can be accessed and worked with in appropriate ways. In the context of the present environment, the data structure may be selected or otherwise designed to store data for the purpose of working on the data with various algorithms executed by components of the executable instructions, depending upon the application thereof for the respective device 200. It is recognized that the terminology of a table/database is interchangeable with that of a data structure with reference to the components of the environment.

In an alternative embodiment, referring to FIGS. 1,2,3,4,5,6,7 a knitted garment 10 is configured for sensing movement of an adjacent underlying body portion 14 of a wearer 12 of the garment 10 via one or more sensors 18, the garment comprises: a garment body including a plurality of fibres knitted together to form a layer 23 of the garment, the garment layer 23 for positioning adjacent to the underlying body portion 14 when worn by the wearer 12; one or more electrical connectors 21 attached to the garment body 23, the one or more electrical connectors 21 for facilitating receipt and transmission of electrical signals between a controller 16 and the one or more sensors 18 when the controller 16 is connected to the one or more electrical connectors 21; a conductive pathway 19 consisting of one or more conductive fibres incorporated in the garment layer 23 by knitting as part of the plurality of fibres, the conductive pathway 19 electrically connected to the one or more electrical connectors 21 and to the one or more sensors 18; each of the one or more sensors 18 incorporated in the garment layer 23 by knitting as part of the plurality of fibres comprising the body layer 23, each of the one or more sensors 18 knitted using a plurality of conductive fibres electrically connected to the one or more conductive fibres of the conductive pathway 19; wherein the controller 16 is configured to measure changes in at least one of resistance or capacitance of the one or more sensors 18 as representative of the movement of the underlying body portion 14 when positioned adjacent to the one or more sensors 18. Further, the knitted garment 10 is such that the movement is representative of a change in the underlying body portion 14 selected from the group consisting of: a change in body posture associated with the underlying body portion 14 of the wearer 12; a change in bend of a body joint 14 associated with the underlying body portion 14 of the wearer 12; a change in volume of the underlying body portion 14 of the wearer 12; a change in width of the underlying body portion 14: and elongation or contraction of the underlying body portion 14 of the wearer 12.

Further, the knitted garment 10 is such that the garment body layer 23 form is selected from the group consisting of: a band 10 for wearing by the wearer 12 around the underlying body portion 14; a garment 10 for positioning on a torso 14 of the wearer 12; a garment 10 for positioning on a limb 14 of the wearer 12; a garment 10 for positioning on a foot 14 of the wearer 12; a garment 10 for positioning on a hand 14 of the wearer 12; and a garment 10 for positioning over a pelvic region 14 of the wearer 12.

Further, the knitted garment 10 is such that the garment body layer 23 can include a first region 24 of the garment layer 23 containing the one or more sensors 18 and a second region 22 of the garment layer 23 adjacent to the first region 24, the first region 24 having a lower (e.g. less stretch or flexibility) degree of elasticity reflected by the plurality of fibres therein relative to a degree of elasticity reflected by the plurality of fibres in the second region 22; wherein the second region 22 contains non-conductive fibres for electrically insulating the one or more sensors 18 from another conductive region 24 in the garment layer 23.

Further, the knitted garment 10 further comprising the plurality of fibres in the first region 24 provide a thickness of the garment layer 23 greater than a thickness of the plurality of fibres in the second region 22.

Further, the knitted garment 10 further comprising a knit type of the plurality of the fibres in the first region 24 is different from a knit type of the plurality of fibres in the second region 22, such that said difference is a factor providing the first region 24 having the lower degree of elasticity reflected by the plurality of fibres therein relative to the degree of elasticity reflected by the plurality of fibres in the second region 22. The knitted garment 10 is such that the plurality of the fibres in the first region 24 can include both the plurality of conductive fibres connected to the conductive pathway 19 and non-conductive fibres, meaning the sensor 18 includes both conductive and non-conductive fibres.

Further, the knitted garment 10 is such that the plurality of the fibres in the first region 24 can have a higher thread (e.g. knit) density (i.e. threads per inch) than the plurality of fibres in the second region 22, reflecting that the fibres of the sensor 18 in the first region 24 are included in the higher thread density. Also, the knitted garment can be such that the plurality of the fibres themselves in the first region 24 can have a lower degree of elasticity than the plurality of fibres in the second region 22.

It is recognised that the knitted garment 10 can be such that the change in the at least one of resistance or capacitance of the one or more sensors reflects a change in shape of the plurality of conductive fibres of the one or more sensors 18 due to the movement of the underlying body portion 14, the shape representing a surface area portion 24 of the garment layer 23 representing the one or more sensors 18. For example, the change in shape can reflect a change in length in the plurality of conductive fibres of the one or more sensors 18, the length representing a longitudinal axis of the one or more sensors 18 along a physical orientation of the conductive pathway 19. Alternatively, the change in shape can reflect a change in width in the plurality of conductive fibres of the one or more sensors 18, the width representing a transverse axis of the one or more sensors 18 lateral to a physical orientation of the conductive pathway 19. Alternatively, the change in shape can reflect a change in thickness in the plurality of conductive fibres of the one or more sensors 18, the thickness representing a transverse axis of the one or more sensors 18 as a thickness of the layer 23 lateral to a physical orientation of the conductive pathway 19.

For example, the garment layer 23 can comprise a first sensor 18 of the one or more sensors 18 in a first location 24 in the garment layer 23 and a second sensor 18 of the one or more sensors 18 in a second location 24 in the garment layer 23, the first location 24 spaced apart from the second location 24 in the garment layer 23, such that both the first sensor 18 and the second sensor 18 are connected to the one or more electrical connectors 21 for sensing the movement in the same adjacent underlying body portion 14. Further, the knitted garment 10 can further comprise a first sensor 18 of the one or more sensors 18 in a first location 24 in the garment layer 23 and a second sensor 18 of the one or more sensors 18 in a second location 24 in the garment layer 23, the first location 24 spaced apart from the second location 24 in the garment layer 23, such that both the first sensor 18 and the second sensor 18 are connected to the one or more electrical connectors 21, the first sensor 18 for sensing the movement in the underlying body portion 14 and the second sensor 18 for sensing movement in a second underlying body portion 14 separate from the underlying body portion 14. For example, the first location 24 and the second location 24 are opposed to one another on opposite sides of the garment 10 representing opposite sides of the body of the wearer 12. For example, the first location 24 and the second location 24 are adjacent to one another on a same side of the garment 10 representing on a same side of the body of the wearer 12.

For example, the knitted garment 10 is such that the change in the underlying body portion 14 can be associated with an activity selected from the group consisting of: a sport; monitored range of motion (e.g. gait) of the underlying body portion 14 (e.g. legs); and/or monitored shape (e.g. swelling) of the underlying body portion 14.

As such, the knitted garment 10 can be such that the plurality of fibres of the garment body 23 can be formed as a one panel 24 of a plurality of panels 22,24 comprising the knitted garment 10, recognising that the panels 22 are those panels which do not contain sensors 18 connected to the controller device 16. For example, the knitted garment 10 can be such that the garment body 23 is knit as a compression garment. For example, the plurality of fibres can include non-conductive fibre material selected from the group consisting of: nylon: cotton; spandex: polyester; and/or silk. For example, the knitted garment 10 is such that the plurality of conductive fibres can include conductive fibre material selected from the group consisting of: stainless steel; silver; aluminum: copper; and/or gold. The one or more sensors 18 can have their plurality of conductive fibres (and optionally non-conductive fibres) knitted/woven into a specified thread pattern (e.g. meander band pattern) integral with the other fibres knitted/woven in the garment body layer 23.

Figure 3:
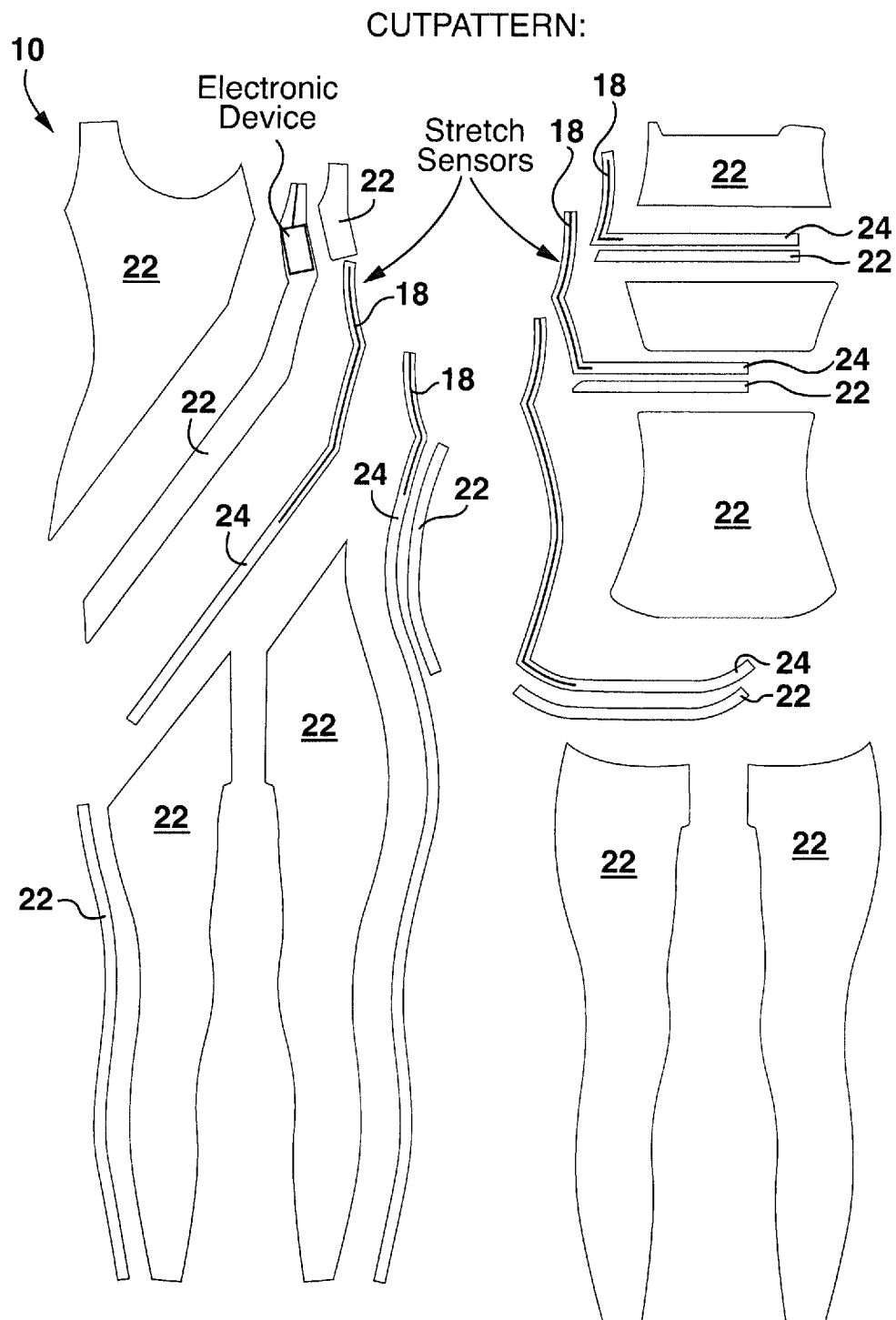
FIG. 3 is a further embodiment of a panelled garment of the garment of FIG. 1 showing garment regions.

Referring to FIG. 3, two or more sections 22,24 of the garment 10 (each comprising a network or networks of fibres or yarn (e.g. containing electrical conducting components 18,19 and a non-conducting section composed only on insulative or non-conducting fibres/yam) can be integrated into a common layer 23 by interlacing at least one fibre or yarn of each section 22,24 with at least one fibre or yarn of an adjacent section 22,24 It is recognised that the sections 22,24 can be provided as separate panels stitched together before or after manufacture or can be provided as a seamless connection between the sections 22,24 at the time of manufacture. In any event, it is recognised that the sections 22,24 can be contained within the same layer 23 rather in overlapping layers.

It should be noted that herein, garment body layer 23 can refer to any material made or formed by manipulating natural or artificial fibres to interlace to create an organized network of fibres. Generally, garments 10 are formed using yarn, where yarn can refer to a long continuous length of a series of fibres that have been interlocked (i.e. fitting into each other, as if twined together, or twisted together). Herein, the terms fibre and yarn are used interchangeably. Fibres or yarns can be manipulated to form the garment 10 according to any method that provides an interlaced organized network of fibres comprising the layer 23, including but not limited to weaving, knitting, sew and cut, crocheting, knotting and felting, weft and waft. Exemplary structures of garment body layer 23 formed by knitting and weaving are provided in FIGS. 10 and 11, respectively.

Different sections 22,24 of the garment 10 can be integrally formed into a common layer 23 to utilize different structural properties of different types of fibres. For example, conductive fibres can be manipulated to form networks of conductive fibres and non-conductive fibres can be manipulated to form networks of non-conductive fibers. These networks of fibres can comprise different sections 22,24 of the garment 10 by integrating the networks of fibres into a common layer 23 of the garment 10. It is recognised that both non-conductive fibres and conductive fibres can be combined in an interlaced pattern in the sections 24 containing the components 18,19 as well as in the sections 22 absent the components 18,19, as long as any conductive fibres in the sections 22 are not in contact with the components 18,19 of section(s) 24, as the non-conductive fibre properties of section(s) 22 are intended to insulate the conductive sections 24 form one another in the case where there are multiple sections 24.

Figure 10:
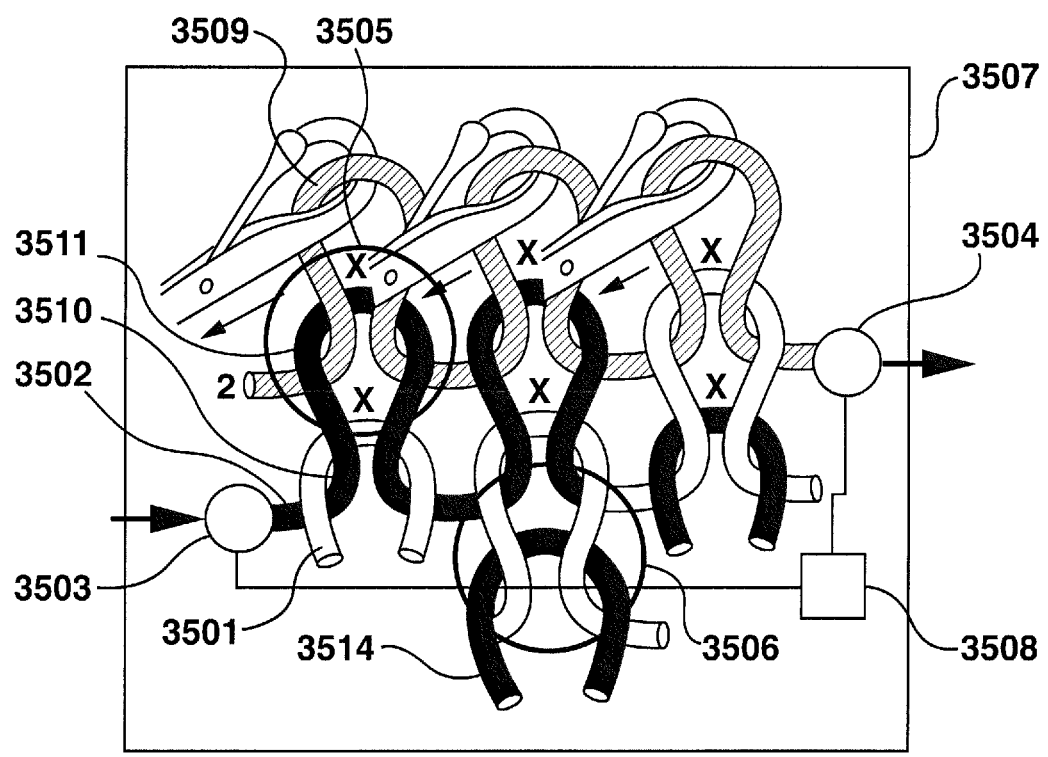
FIG. 10 is an example of interlacing of the plurality of fibres of the garment body layer of the garment of FIG. 1.
Figure 11:
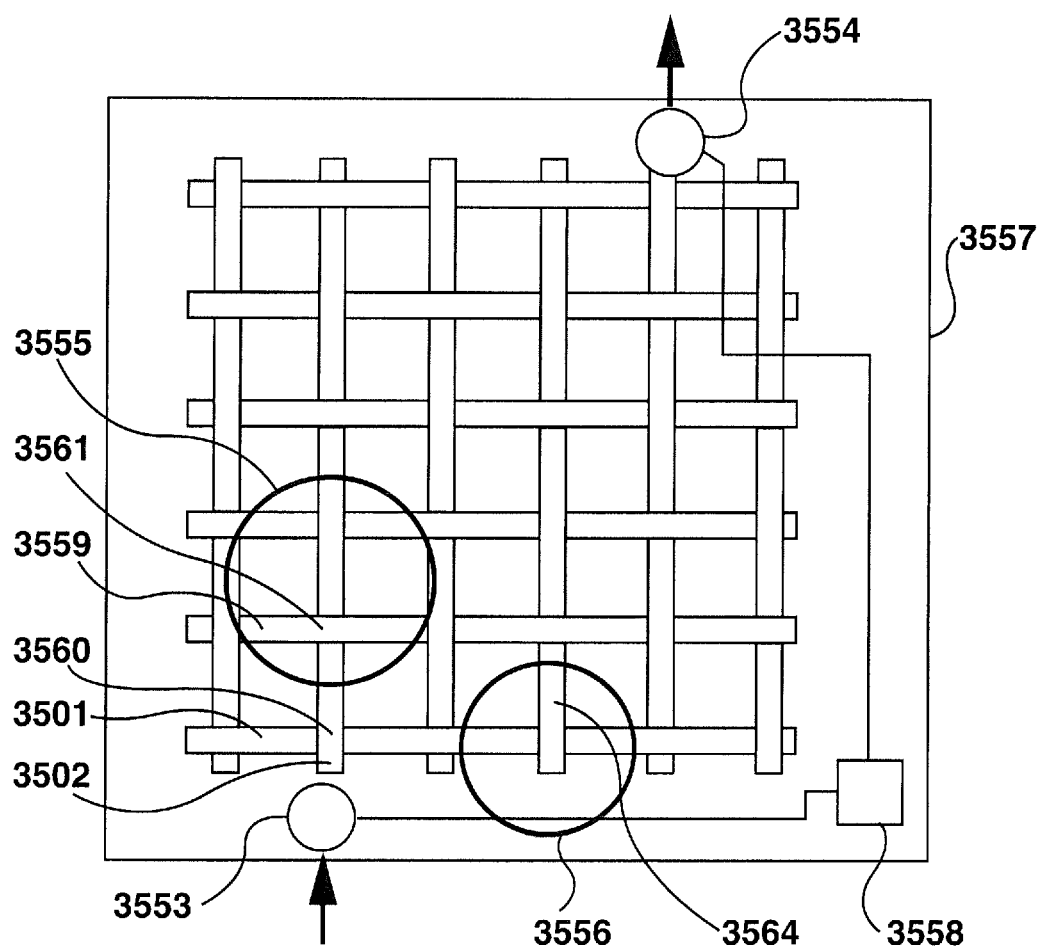
FIG. 11 is a further embodiment of interlacing of the plurality of fibres of the garment body layer of the garment of FIG. 1.

It should also be noted that herein, "interlaced". "integrated" or "embedded" refer to fibres (either artificial or natural) crossing over and/or under one another in an organized fashion, typically alternately over and under one another, in a common layer 23. When interlaced (also referred to as integrated or embedded), adjacent fibres touch each other at intersection points (e.g. points where one fibre crosses over or under another fibre). In one example, first fibres extending in a first direction can be interlaced with second fibres extending laterally or transverse to the fibres extending in the first connection. In another example, the second fibres can extend laterally at 90° from the first fibres when interlaced with the first fibres. Interlaced fibres extending in a common sheet can be referred to as a network of fibres. FIGS. 10 and 11, described below, provide exemplary embodiments of interlaced fibres.

"Integrated" can also refer to combining, coordinating or otherwise bringing together separate elements so as to provide a harmonious, consistent, interrelated whole. In the context of the garment, the garment can have various sections comprising networks of fibres with different structural properties. For example, the garment 10 can have a section comprising a network of conductive fibres and a section comprising a network of non-conductive fibres. Two or more sections comprising networks of fibres are said to be "integrated" together into a textile (or "integrally formed") when at least one fibre of one network is interlaced with at least one fibre of the other network such that the two networks form a common layer of the garment 10. Further, when integrated, two sections of a garment 10 can also be described as being substantially inseparable from the garment 10. Here, "substantially inseparable" refers to the notion that separation of the sections 22,24, as well as internally to the sections 22,24 their network of fibres, of the garment 10 from each other results in disassembly or destruction of the garment 10 itself. For example, fibres of the fibre network within a given section 22,24 are considered inseparable.

In the embodiments, the fibres of the electric conductive pathway 19 can be integrated with non-conductive fibres into a common layer 23. "Layer" refers to a thickness of the garment 10. Integrating two sections 22,24 (or segments of sections) into a common layer 23 means that at least a portion of each of the two sections 22,24 or segments (e.g. at least some of the fibres comprising the network of fibres of each section or segment 22,24) have a thickness and are interlaced together to attach together at the respective portions of the thickness. For example, each of electric pathway 19 fibres and a network of non-conductive fibres adjacent to the electric pathway 19 can be made loops of knitted non-conductive fibres. It should be noted that electric pathway 19 can comprise both conductive and non-conductive fibres, and non-conductive section 22 adjacent to the electric pathway 19 can also comprise both non-conductive fibres and conductive fibres, so long as the conductive fibres of the electric pathway 19 are not electrically connected to the conductive fibres of non-conductive section 22. Non-conductive section 22 can therefore be considered as an insulator to the electric pathway 19.

Two conductive fibres are "electrically contacting" when an electric current can be transmitted between the fibres (e.g. the adjacent fibres are touching). A conductive fibre is said to be "electrically contacting" an adjacent conductive fibre at an intersection point (see also FIGS. 10 and 11, below).

Electrically conductive sensors 18 can configured to have varying resistances, where resistance over an electrically conductive network of fibres of the sensor 18 can be controlled at least by varying the length of the sensor 18, the width of the sensor 18 and/or the density of sensor 18. The density of a sensor 18 refers to the mass of the sensor 18 per unit volume of the sensor 18. Therefore, for example, increasing the total number of loops of conductive fibres within a unit area of an electrically conductive sensor 18 increases the density of the electrically conductive sensor 18. As a further example, resistance increases as the width of a sensor 18 decreases. Resistance can also be controlled by varying the conductive material in the conductive fibre and the length of the conductive fibre (e.g. where sensor 18 being longer than another sensor 18 will have a higher resistance for a same current and voltage).

In one example embodiment, knitting can be used to integrate different sections of a garment 10 into a common layer 23 (e.g. a conductive pathway 19, a sensor 18 and non-conductive sections). Knitting comprises creating multiple loops of fibre or yarn, called stitches, in a line or tube. In this manner, the fibre or yarn in knitted fabrics follows a meandering path (e.g. a course), forming loops above and below the mean path of the yarn. These meandering loops can be easily stretched in different directions. Consecutive rows of loops can be attached using interlocking loops of fibre or yarn. As each row progresses, a newly created loop of fibre or yarn is pulled through one or more loops of fibre or yarn from a prior row of the layer 23.

In another example embodiment, weaving can be used to integrate different sections of a garment 10 into a common layer 23 (e.g. a conductive pathway 19, sensor 18 and non-conductive sections). Weaving is a method of forming a garment 10 in which two distinct sets of yarns or fibres are interlaced at a specified (e.g. right) angles to form the layer 23 of the garment 10.

FIG. 10 shows an exemplary knitted configuration of a network of electrically conductive fibres 3505 in, for example, a segment of an electric component (e.g. 18,19). In this embodiment, an electric signal (e.g. current) is transmitted to conductive fibre 3502 from a power source (not shown) through a first connector 3505 (e.g. connector 21 see FIG. 4), as controlled by a controller 3508 (e.g. controller 16—see FIG. 4). The electric signal is transmitted along the electric pathway along conductive fibre 3502 past non-conductive fibre 3501 at junction point 3510. The electric signal is not propagated into non-conductive fibre 3501 at junction point 3510 because non-conductive fibre 3501 cannot conduct electricity. Junction point 3510 can refer to any point where adjacent conductive fibres and non-conductive fibres are contacting each other (e.g. touching). In the embodiment shown in FIG. 10, non-conductive fibre 3501 and conductive fibre 3502 are shown as being interlaced by being knitted together. Knitting is only one exemplary embodiment of interlacing adjacent conductive and non-conductive fibres.

It should be noted that non-conductive fibres forming non-conductive network 3506 can also be interlaced (e.g. by knitting, etc.). Non-conductive network 3506 can comprise non-conductive fibres (e.g. 3501) and conductive fibres (e.g. 3514) where the conductive fibre 3514 is electrically connected to conductive fibres transmitting the electric signal (e.g. 3502).

In the embodiment shown in FIG. 10, the electric signal continues to be transmitted from junction point 3510 along conductive fibre 3502 until it reaches connection point 3511. Here, the electric signal propagates laterally (e.g. transverse) from conductive fibre 3502 into conductive fibre 3509 because conductive fibre 3509 can conduct electricity. Connection point 3511 can, refer to any point where adjacent conductive fibres (e.g. 3502 and 3509) are contacting each other (e.g. touching). In the embodiment shown in FIG. 10, conductive fibre 3502 and conductive fibre 3509 are shown as being interlaced by being knitted together. Again, knitting is only one exemplary embodiment of interlacing adjacent conductive fibres.

The electric signal continues to be transmitted from connection point. 3511 along the electric pathway to connector 3504. At least one fibre of network 3505 is attached to connector 3504 (e.g. connector 21 see FIG. 4) to transmit the electric signal from the electric component 18,19 (e.g. network 3505) to connector 3504. Connector 3504 is connected to a power source (not shown) to complete the electric circuit.

FIG. 11 shows an exemplary woven configuration of a network of electrically conductive fibres 3555. In this embodiment, an electric signal (e.g. current) is transmitted to conductive fibre 3552 from a power source (not shown) through a first connector 3555 (e.g. connector 21 see FIG. 4), as controlled by a controller 3558 (e.g. controller 16 see FIG. 4). The electric signal is transmitted along the electric component 18,19 along conductive fibre 3552 past non-conductive fibre 3551 at junction point 3560. The electric signal is not propagated into non-conductive fibre 3551 at junction point 3560 because non-conductive fibre 3551 cannot conduct electricity. Junction point 3560 can refer to any point where adjacent conductive fibres and non-conductive fibres are contacting each other (e.g. touching). In the embodiment shown in FIG. 11, non-conductive fibre 3551 and conductive fibre 3502 are shown as being interlaced by being woven together. Weaving is only one exemplary embodiment of interlacing adjacent conductive and non-conductive fibres.

It should be noted that non-conductive fibres forming non-conductive network 3556 are also interlaced (e.g. by weaving, etc.). Non-conductive network 3556 can comprise non-conductive fibres (e.g. 3551 and 3564) and can also comprise conductive fibres that are not electrically connected to conductive fibres transmitting the electric signal.

The electric signal continues to be transmitted from junction point 3560 along conductive fibre 3502 until it reaches connection point 3561. Here, the electric signal propagates laterally (e.g. transverse) from conductive fibre 3552 into conductive fibre 3559 because conductive fibre 3559 can conduct electricity. Connection point 3561 can refer to any point where adjacent conductive fibres (e.g. 3552 and 3559) are contacting each other (e.g. touching). In the embodiment shown in FIG. 11, conductive fibre 3552 and conductive fibre 3559 are shown as being interlaced by being woven together. Again, weaving is only one exemplary embodiment of interlacing adjacent conductive fibres.

Figure 4:
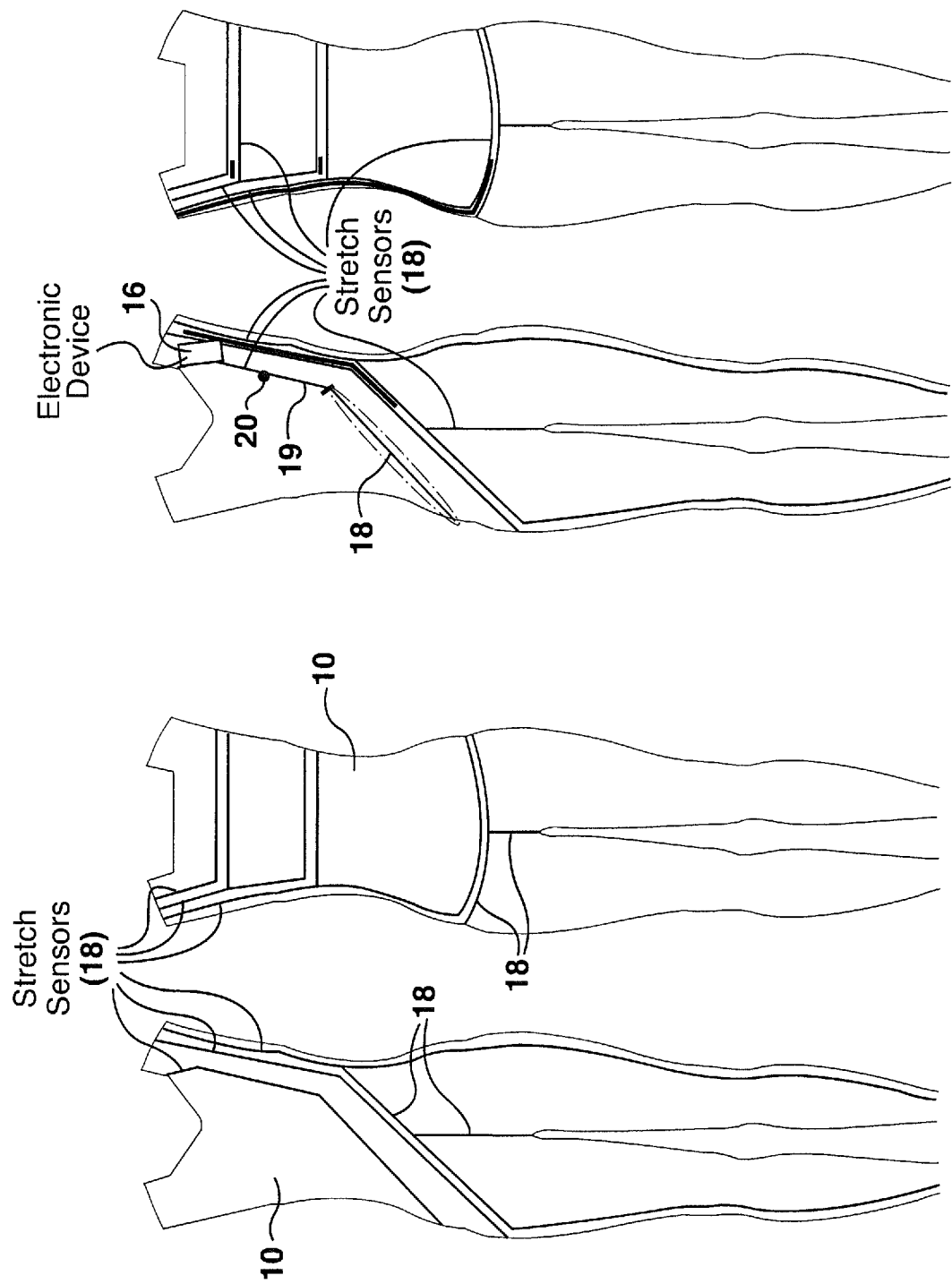
FIG. 4 shows a further embodiment of the garment of FIG. 2 with a controlled connected to the sensors.

The electric signal continues to be transmitted from connection point 3561 along the electric pathway through a plurality of connection points 3561 to connector 3554 (e.g. connector 21 see FIG. 4). At least one conductive fibre of network 3555 is attached to connector 3554 to transmit the electric signal from the electric component 18,19 (e.g. network 3555) to connector 3554 (e.g. connector 21 see FIG. 4). Connector 3554 (e.g. connector 21 see FIG. 4) can be connected to a power source (not shown) to complete the electric circuit.

While various specific embodiments have been illustrated and described herein, those of ordinary skill in the art will envision numerous modifications without significantly departing from the spirit of the present disclosure, and the scope of protection is intended to be limited only by the scope of the accompanying claims.

What is claimed is:

1. A knitted garment configured for sensing movement of an adjacent underlying body portion of a wearer of the garment via one or more sensors, the garment comprising:

a garment body including fibres knitted together to form a layer of the garment, the garment layer for positioning adjacent to the underlying body portion when worn by the wearer;

one or more electrical connectors attached to the garment body, the one or more electrical connectors for facilitating receipt and transmission of electrical signals between a controller and the one or more sensors when the controller is connected to the one or more electrical connectors;

a conductive pathway consisting of one or more conductive fibres incorporated in the garment layer by knitting as part of the fibres, the conductive pathway electrically connected to the one or more electrical connectors and to the one or more sensors;

a first region in the garment layer having a first plurality of fibres including conductive fibres comprising the one or more sensors and a second region in the garment layer adjacent to the first region, the second region having a second plurality of fibres as non-conductive fibres comprising an insulative region of the garment layer surrounding the first region, the first plurality of fibres interlaced with one another to have a first degree of elasticity reflected by the first plurality of fibres as a group therein that is lower than a second degree of elasticity reflected by the second plurality of fibres as a group therein; wherein the non-conductive fibres of the second region are for electrically insulating the one or more sensors from another sensor in the garment layer also adjacent to the second region;

each of the one or more sensors incorporated in the garment layer by knitting as part of the fibres, each of the one or more sensors knitted including the conductive fibres in order to electrically connect to the one or more conductive fibres of the conductive pathway;

wherein the controller is configured to measure changes in at least one of resistance or capacitance of the one or more sensors as representative of the movement of the underlying body portion when positioned adjacent to the one or more sensors.

2. The knitted garment of claim 1, wherein the movement is representative of a change in the underlying body portion selected from the group consisting of: a change in body posture associated with the underlying body portion of the wearer; a change in bend of a body joint associated with the underlying body portion of the wearer; a change in volume of the underlying body portion of the wearer; and elongation or contraction of the underlying body portion of the wearer.

3. The knitted garment of claim 2, wherein the change in the underlying body portion is associated with an activity selected from the group consisting of: a sport; monitored range of motion (e.g. gait) of the underlying body portion; and monitored shape (e.g. swelling) of the underlying body portion.

4. The knitted garment of claim 1, wherein the garment body is selected from the group consisting of: a band for wearing by the wearer around the underlying body portion; a garment for positioning on a torso of the wearer; a garment for positioning on a limb of the wearer; a garment for positioning on a foot of the wearer; a garment for positioning on a hand of the wearer; and a garment for positioning over a pelvic region of the wearer.

5. The knitted garment of claim 1 further comprising the first plurality of fibres in the first region provide a thickness of the garment layer greater than a thickness of the second plurality of fibres in the second region.

6. The knitted garment of claim 1 further comprising a knit type of the first plurality of the fibres in the first region is different from a knit type of the second plurality of fibres in the second region, such that said difference is a factor providing said first region having the lower degree of elasticity reflected by the first plurality of fibres therein relative to the degree of elasticity reflected by the second plurality of fibres in the second region.

7. The knitted garment of claim 6, wherein the first plurality of the fibres in the first region includes both the conductive fibres connected to the conductive pathway and further non-conductive fibres.

8. The knitted garment of claim 1, wherein the first plurality of the fibres in the first region have a higher knit density than the second plurality of fibres in the second region.

9. The knitted garment of claim 1, wherein the first plurality of the fibres themselves in the first region have a lower degree of elasticity than the second plurality of fibres in the second region.

10. The knitted garment of claim 1, wherein said change in said at least one of resistance or capacitance of the one or more sensors reflects a change in shape of the conductive fibres of the one or more sensors due to the movement of the underlying body portion, the shape representing a surface area portion of the garment layer representing the one or more sensors.

11. The knitted garment of claim 10, wherein said change in shape reflects a change in length in the plurality of conductive fibres of the one or more sensors, the length representing a longitudinal axis of the one or more sensors along a physical orientation of the conductive pathway.

12. The knitted garment of claim 10, wherein said change in shape reflects a change in width in the plurality of conductive fibres of the one or more sensors, the width representing a transverse axis of the one or more sensors lateral to a physical orientation of the conductive pathway.

13. The knitted garment of claim 1 further comprising a first sensor of the one or more sensors in a first location in the garment layer and a second sensor of the one or more sensors in a second location in the garment layer, the first location spaced apart from the second location in the garment layer, such that both the first sensor and the second sensor are connected to the one or more electrical connectors for sensing the movement in the same adjacent underlying body portion.

14. The knitted garment of claim 13, wherein the first location and the second location are opposed to one another on opposite sides of the garment body.

15. The knitted garment of claim 13, wherein the first location and the second location are adjacent to one another on a same side of the garment body.

16. The knitted garment of claim 1 further comprising a first sensor of the one or more sensors in a first location in the garment layer and a second sensor of the one or more sensors in a second location in the garment layer, the first location spaced apart from the second location in the garment layer, such that both the first sensor and the second sensor are connected to the one or more electrical connectors, the first sensor for sensing the movement in the underlying body portion and the second sensor for sensing movement in a second underlying body portion separate from the underlying body portion.

17. The knitted garment of claim 16, wherein the first location and the second location are opposed to one another on opposite sides of the garment body.

18. The knitted garment of claim 16, wherein the first location and the second location are adjacent to one another on a same side of the garment body.

19. The knitted garment of claim 1, wherein the fibres of the garment body are formed as a seamless knit garment type.

20. The knitted garment of claim 1, wherein the fibres of the garment body are formed as a one panel of a plurality of panels comprising the knitted garment.

21. The knitted garment of claim 1, wherein the garment body is knit as a compression garment.

22. The knitted garment of claim 1, wherein the fibres includes non-conductive fibre material selected from the group consisting of: nylon; cotton; spandex; polyester; and silk.

23. The knitted garment of claim 1, wherein the conductive fibres include conductive fibre material selected from the group consisting of: stainless steel; silver; aluminum; copper; and gold.

24. The knitted garment of claim 1, wherein the one or more sensors have the conductive fibres kitted into a specified thread pattern (e.g. meander band pattern).

* * * * *